(12) United States Patent
Leopold et al.

(10) Patent No.: US 9,107,669 B2
(45) Date of Patent: Aug. 18, 2015

(54) BLOOD VESSEL OCCLUSION

(71) Applicant: Artventive Medical Group, Inc., San Marcos, CA (US)

(72) Inventors: Andrew Leopold, Hawthorn Woods, IL (US); Leon Rudakov, San Marcos, CA (US); Kelly Jensen, Chicago, IL (US)

(73) Assignee: ArtVentive Medical Group, Inc., San Marcos, CA (US)

( * ) Notice: Subject to any disclaimer, the term of this patent is extended or adjusted under 35 U.S.C. 154(b) by 0 days.

(21) Appl. No.: 14/281,797

(22) Filed: May 19, 2014

(65) Prior Publication Data

US 2014/0257369 A1    Sep. 11, 2014

Related U.S. Application Data

(63) Continuation of application No. 13/828,974, filed on Mar. 14, 2013.

(60) Provisional application No. 61/761,195, filed on Feb. 5, 2013.

(51) Int. Cl.
*A61B 1/267* (2006.01)
*A61B 17/12* (2006.01)

(52) U.S. Cl.
CPC ..... *A61B 17/12109* (2013.01); *A61B 17/12145* (2013.01); *A61B 2017/12054* (2013.01)

(58) Field of Classification Search
CPC .............. A61B 17/12109; A61B 17/12145; A61B 2017/12054; A61B 2017/1205–2017/12095; A61B 17/12022; A61B 17/12131; A61F 2/95; A61F 2/962–2/97; A61F 2002/9505–2002/9534; A61F 2002/9665; A61F 6/20

USPC ................ 606/191–200, 108; 623/1.11–1.35; 128/831, 843

See application file for complete search history.

(56) References Cited

U.S. PATENT DOCUMENTS

| | | |
|---|---|---|
| 3,805,767 A | 4/1974 | Erb |
| 3,868,956 A | 3/1975 | Alfidi et al. |

(Continued)

FOREIGN PATENT DOCUMENTS

| | | |
|---|---|---|
| CN | 2527227 Y | 12/2002 |
| EP | 1166721 A2 | 1/2002 |

(Continued)

OTHER PUBLICATIONS

Aydogan, Transcatheter Embolization Treatment of Coronary Arteriovenous Fistulas, Asian Cardiovascular & Thoracic Annals, 2003, pp. 63-67, vol. 11, No. 1.

(Continued)

*Primary Examiner* — Amy R Weisberg
(74) *Attorney, Agent, or Firm* — Nathan S. Smith; McDermott Will & Emery LLP

(57) ABSTRACT

An occlusion device delivery system can deliver an expandable coiled implant using a catheter. A distal portion of the catheter has proximal and distal apertures extending through a wall of the catheter. The expandable coiled implant is wound about the distal portion and has a proximal section that extends within the proximal aperture and a distal section that can extend radially within the distal aperture. Further, the system has an elongate member that extends through the lumen and engages and radially restrains the at least one of the proximal and distal sections within its respective aperture while engaged with the member.

23 Claims, 9 Drawing Sheets

(56) References Cited

U.S. PATENT DOCUMENTS

| | | | | |
|---|---|---|---|---|
| 3,918,431 | A | 11/1975 | Sinnreich | |
| 4,013,063 | A | 3/1977 | Bucalo | |
| 4,245,623 | A | 1/1981 | Erb | |
| 4,553,545 | A | 11/1985 | Maass et al. | |
| 4,649,922 | A | 3/1987 | Wiktor | |
| 4,682,592 | A | 7/1987 | Thorsgard | |
| 4,705,517 | A | 11/1987 | DiPisa, Jr. | |
| 4,706,671 | A | 11/1987 | Weinrib | |
| 4,733,665 | A | 3/1988 | Palmaz | |
| 4,739,762 | A | 4/1988 | Palmaz | |
| 4,768,507 | A | 9/1988 | Fischell et al. | |
| 4,776,337 | A | 10/1988 | Palmaz | |
| 4,800,882 | A * | 1/1989 | Gianturco | 606/194 |
| 4,827,946 | A | 5/1989 | Kaali et al. | |
| 4,913,141 | A * | 4/1990 | Hillstead | 623/1.11 |
| 4,969,890 | A | 11/1990 | Sugita et al. | |
| 5,037,427 | A | 8/1991 | Harada et al. | |
| 5,065,751 | A | 11/1991 | Wolf | |
| 5,089,005 | A | 2/1992 | Harada | |
| 5,102,417 | A | 4/1992 | Palmaz | |
| 5,147,370 | A | 9/1992 | McNamara et al. | |
| 5,234,437 | A | 8/1993 | Sepetka | |
| 5,242,451 | A | 9/1993 | Harada et al. | |
| 5,242,452 | A | 9/1993 | Inoue | |
| 5,304,198 | A | 4/1994 | Samson | |
| 5,324,306 | A | 6/1994 | Makower et al. | |
| 5,334,210 | A | 8/1994 | Gianturco | |
| 5,342,387 | A | 8/1994 | Summers | |
| 5,372,600 | A * | 12/1994 | Beyar et al. | 623/1.11 |
| 5,417,708 | A | 5/1995 | Hall et al. | |
| 5,474,089 | A | 12/1995 | Waynant | |
| 5,476,505 | A * | 12/1995 | Limon | 623/1.11 |
| 5,499,995 | A | 3/1996 | Teirstein | |
| 5,536,274 | A | 7/1996 | Neuss | |
| 5,562,641 | A | 10/1996 | Flomenblit et al. | |
| 5,562,698 | A | 10/1996 | Parker | |
| 5,607,445 | A | 3/1997 | Summers | |
| 5,656,036 | A | 8/1997 | Palmaz | |
| 5,674,287 | A | 10/1997 | Slepian et al. | |
| 5,693,083 | A | 12/1997 | Baker et al. | |
| 5,725,552 | A | 3/1998 | Kotula et al. | |
| 5,733,329 | A | 3/1998 | Wallace et al. | |
| 5,772,668 | A * | 6/1998 | Summers et al. | 623/1.11 |
| 5,782,860 | A | 7/1998 | Epstein et al. | |
| 5,797,952 | A | 8/1998 | Klein | |
| 5,797,953 | A | 8/1998 | Tekulve | |
| 5,830,222 | A | 11/1998 | Makower | |
| 5,842,621 | A | 12/1998 | Gschwind | |
| 5,868,782 | A | 2/1999 | Frantzen | |
| 5,902,266 | A | 5/1999 | Leone et al. | |
| 5,922,009 | A | 7/1999 | Epstein et al. | |
| 5,925,063 | A | 7/1999 | Khosravi | |
| 5,925,074 | A | 7/1999 | Gingras et al. | |
| 5,928,260 | A | 7/1999 | Chin et al. | |
| 5,944,738 | A | 8/1999 | Amplatz et al. | |
| 5,954,766 | A | 9/1999 | Zadno-Azizi et al. | |
| 5,957,929 | A | 9/1999 | Brenneman | |
| 5,979,446 | A | 11/1999 | Loy | |
| 6,010,517 | A * | 1/2000 | Baccaro | 606/151 |
| 6,019,779 | A * | 2/2000 | Thorud et al. | 606/198 |
| 6,024,765 | A | 2/2000 | Wallace et al. | |
| 6,056,770 | A | 5/2000 | Epstein et al. | |
| 6,059,825 | A | 5/2000 | Hobbs et al. | |
| 6,117,157 | A | 9/2000 | Tekulve | |
| 6,123,715 | A | 9/2000 | Amplatz | |
| 6,168,622 | B1 | 1/2001 | Mazzocchi | |
| 6,190,353 | B1 | 2/2001 | Makower et al. | |
| 6,210,338 | B1 | 4/2001 | Afremov et al. | |
| 6,214,042 | B1 | 4/2001 | Jacobsen et al. | |
| 6,241,678 | B1 | 6/2001 | Afremov et al. | |
| 6,241,758 | B1 | 6/2001 | Cox | |
| 6,245,090 | B1 | 6/2001 | Gilson et al. | |
| 6,248,122 | B1 | 6/2001 | Klumb et al. | |
| 6,283,983 | B1 | 9/2001 | Makower et al. | |
| 6,334,864 | B1 | 1/2002 | Amplatz et al. | |
| 6,346,118 | B1 | 2/2002 | Baker et al. | |
| 6,361,558 | B1 | 3/2002 | Hieshima et al. | |
| 6,368,339 | B1 | 4/2002 | Amplatz | |
| 6,371,953 | B1 | 4/2002 | Beyar et al. | |
| 6,371,979 | B1 * | 4/2002 | Beyar et al. | 623/1.12 |
| 6,402,760 | B1 | 6/2002 | Fedida | |
| 6,402,772 | B1 | 6/2002 | Amplatz et al. | |
| 6,432,116 | B1 | 8/2002 | Callister et al. | |
| 6,432,127 | B1 | 8/2002 | Kim et al. | |
| 6,447,531 | B1 | 9/2002 | Amplatz | |
| 6,451,025 | B1 * | 9/2002 | Jervis | 606/108 |
| 6,454,780 | B1 | 9/2002 | Wallace | |
| 6,464,712 | B1 * | 10/2002 | Epstein et al. | 606/213 |
| 6,468,301 | B1 | 10/2002 | Amplatz et al. | |
| 6,506,204 | B2 | 1/2003 | Mazzocchi | |
| 6,533,805 | B1 * | 3/2003 | Jervis | 623/1.11 |
| 6,550,480 | B2 | 4/2003 | Feldman et al. | |
| 6,554,849 | B1 | 4/2003 | Jones et al. | |
| 6,562,064 | B1 | 5/2003 | deBeer | |
| 6,572,643 | B1 | 6/2003 | Gharibadeh | |
| 6,579,303 | B2 | 6/2003 | Amplatz | |
| 6,585,760 | B1 | 7/2003 | Fogarty | |
| 6,599,308 | B2 | 7/2003 | Amplatz | |
| 6,602,271 | B2 | 8/2003 | Adams et al. | |
| 6,616,675 | B1 | 9/2003 | Evard et al. | |
| 6,623,518 | B2 | 9/2003 | Thompson et al. | |
| 6,629,981 | B2 | 10/2003 | Bui et al. | |
| 6,638,243 | B2 | 10/2003 | Kupiecki | |
| 6,638,257 | B2 | 10/2003 | Amplatz | |
| 6,638,293 | B1 | 10/2003 | Makower et al. | |
| 6,645,237 | B2 | 11/2003 | Klumb et al. | |
| 6,656,207 | B2 | 12/2003 | Epstein et al. | |
| 6,660,020 | B2 | 12/2003 | Wallace et al. | |
| 6,660,032 | B2 * | 12/2003 | Klumb et al. | 623/1.13 |
| 6,663,666 | B1 | 12/2003 | Quiachon et al. | |
| 6,682,546 | B2 | 1/2004 | Amplatz | |
| 6,689,148 | B2 | 2/2004 | Sawhney et al. | |
| 6,702,846 | B2 * | 3/2004 | Mikus et al. | 623/1.22 |
| 6,719,781 | B1 | 4/2004 | Kim | |
| 6,790,218 | B2 | 9/2004 | Jayaraman | |
| 6,849,081 | B2 | 2/2005 | Sepetka et al. | |
| 6,872,211 | B2 | 3/2005 | White et al. | |
| 6,890,341 | B2 | 5/2005 | Dieck et al. | |
| 6,899,730 | B1 | 5/2005 | Rivelli, Jr. | |
| 6,936,058 | B2 | 8/2005 | Forde et al. | |
| 6,974,473 | B2 * | 12/2005 | Barclay et al. | 623/1.22 |
| 6,984,244 | B2 | 1/2006 | Perez et al. | |
| 7,001,409 | B2 | 2/2006 | Amplatz | |
| 7,011,671 | B2 | 3/2006 | Welch | |
| 7,144,408 | B2 | 12/2006 | Keegan et al. | |
| 7,152,605 | B2 | 12/2006 | Khairkhahan et al. | |
| 7,220,270 | B2 | 5/2007 | Sawhney et al. | |
| 7,270,668 | B2 | 9/2007 | Andreas et al. | |
| 7,276,077 | B2 | 10/2007 | Zadno-Azizi et al. | |
| 7,294,146 | B2 | 11/2007 | Chew et al. | |
| 7,303,571 | B2 | 12/2007 | Makower et al. | |
| 7,387,641 | B2 | 6/2008 | Schmitt | |
| 7,396,362 | B2 * | 7/2008 | Jervis | 623/1.11 |
| 7,398,780 | B2 | 7/2008 | Callister et al. | |
| 7,458,986 | B2 | 12/2008 | Schmitt | |
| 7,476,232 | B2 * | 1/2009 | Deal | 606/127 |
| 7,582,100 | B2 | 9/2009 | Johnson et al. | |
| 7,597,704 | B2 | 10/2009 | Frazier et al. | |
| 7,604,649 | B2 | 10/2009 | McGuckin, Jr. et al. | |
| 7,632,291 | B2 | 12/2009 | Stephens et al. | |
| 7,647,930 | B2 | 1/2010 | Ginn | |
| 7,651,521 | B2 | 1/2010 | Ton et al. | |
| 7,666,204 | B2 | 2/2010 | Thornton et al. | |
| 7,682,673 | B2 | 3/2010 | Houston et al. | |
| 7,691,124 | B2 | 4/2010 | Balgobin | |
| 7,699,056 | B2 * | 4/2010 | Tran et al. | 128/831 |
| 7,740,616 | B2 | 6/2010 | Smith et al. | |
| 7,771,463 | B2 | 8/2010 | Ton et al. | |
| 7,785,343 | B2 | 8/2010 | Johnson et al. | |
| 7,785,631 | B2 | 8/2010 | Roser et al. | |
| 7,789,860 | B2 | 9/2010 | Brady et al. | |
| 7,789,892 | B2 | 9/2010 | Johnson et al. | |
| 7,803,177 | B2 | 9/2010 | Hartley et al. | |
| 7,854,747 | B2 | 12/2010 | Johnson et al. | |

(56) References Cited

U.S. PATENT DOCUMENTS

| | | |
|---|---|---|
| 7,955,343 B2 | 6/2011 | Makower et al. |
| 7,967,837 B2 | 6/2011 | Vale |
| 7,985,250 B2 | 7/2011 | Kaufmann et al. |
| 7,992,565 B2 | 8/2011 | McGuckin, Jr. et al. |
| 8,016,870 B2 | 9/2011 | Chew et al. |
| 8,016,880 B2 | 9/2011 | Cook et al. |
| 8,043,357 B2 | 10/2011 | Hartley |
| 8,100,958 B2 | 1/2012 | Fischer et al. |
| 8,110,267 B2 | 2/2012 | Houston et al. |
| 8,114,114 B2 | 2/2012 | Belson |
| 8,118,852 B2 | 2/2012 | Melsheimer |
| 8,142,456 B2 | 3/2012 | Rosqueta et al. |
| 8,162,970 B2 | 4/2012 | Gilson et al. |
| 8,226,679 B2 | 7/2012 | Johnson et al. |
| 8,226,704 B2 | 7/2012 | Caro et al. |
| 8,308,754 B2 | 11/2012 | Belson |
| 8,323,305 B2 | 12/2012 | Epstein et al. |
| 8,323,350 B2 | 12/2012 | Nissl |
| 8,328,840 B2 | 12/2012 | Gailloud et al. |
| 8,333,783 B2 | 12/2012 | Braun et al. |
| 8,333,796 B2 | 12/2012 | Tompkins et al. |
| 8,343,167 B2 | 1/2013 | Henson |
| 8,348,994 B2 | 1/2013 | Leopold et al. |
| 8,382,771 B2 | 2/2013 | Gellman et al. |
| 8,382,821 B2 | 2/2013 | Richter |
| 8,398,700 B2 | 3/2013 | Leopold et al. |
| 8,425,549 B2 | 4/2013 | Lenker et al. |
| 8,430,904 B2 | 4/2013 | Belson |
| 8,663,301 B2 | 3/2014 | Riina et al. |
| 2001/0000798 A1 | 5/2001 | Denardo |
| 2001/0007946 A1 | 7/2001 | Lenker et al. |
| 2001/0031981 A1 | 10/2001 | Evans et al. |
| 2001/0037146 A1 | 11/2001 | Lau et al. |
| 2001/0044648 A1 | 11/2001 | Wolinsky et al. |
| 2001/0046518 A1 | 11/2001 | Sawhney |
| 2002/0007206 A1 | 1/2002 | Bui et al. |
| 2002/0091439 A1 | 7/2002 | Baker et al. |
| 2002/0099437 A1 | 7/2002 | Anson et al. |
| 2002/0107565 A1 | 8/2002 | Greenhalgh |
| 2002/0123765 A1 | 9/2002 | Sepetka et al. |
| 2002/0128707 A1 | 9/2002 | Kavteladze et al. |
| 2002/0143362 A1 | 10/2002 | Macoviak et al. |
| 2002/0177855 A1 | 11/2002 | Greene et al. |
| 2002/0198588 A1 | 12/2002 | Armstrong et al. |
| 2003/0114922 A1 | 6/2003 | Iwasaka et al. |
| 2003/0125798 A1 | 7/2003 | Martin |
| 2003/0153972 A1 | 8/2003 | Helmus |
| 2003/0163146 A1 | 8/2003 | Epstein et al. |
| 2003/0171801 A1 | 9/2003 | Bates |
| 2003/0187474 A1 | 10/2003 | Keegan et al. |
| 2003/0187495 A1 | 10/2003 | Cully et al. |
| 2003/0216679 A1 | 11/2003 | Wolf et al. |
| 2003/0229366 A1 | 12/2003 | Reggie et al. |
| 2004/0010282 A1 | 1/2004 | Kusleika |
| 2004/0029994 A1 | 2/2004 | Cheng et al. |
| 2004/0055606 A1 | 3/2004 | Hendricksen et al. |
| 2004/0073252 A1 | 4/2004 | Goldberg et al. |
| 2004/0147869 A1 | 7/2004 | Wolf et al. |
| 2004/0153118 A1 | 8/2004 | Clubb et al. |
| 2004/0158308 A1 | 8/2004 | Hogendijk et al. |
| 2004/0193141 A1 | 9/2004 | Leopold et al. |
| 2004/0220663 A1 | 11/2004 | Rivelli |
| 2004/0225286 A1 | 11/2004 | Elliott |
| 2004/0243219 A1 | 12/2004 | Fischer et al. |
| 2004/0249342 A1 | 12/2004 | Khosravi et al. |
| 2004/0254517 A1 | 12/2004 | Quiroz-Mercado et al. |
| 2004/0260384 A1 | 12/2004 | Allen |
| 2005/0027305 A1 | 2/2005 | Shiu et al. |
| 2005/0033409 A1 | 2/2005 | Burke et al. |
| 2005/0043759 A1 | 2/2005 | Chanduszko |
| 2005/0055079 A1 | 3/2005 | Duran |
| 2005/0055082 A1 | 3/2005 | Ben Muvhar et al. |
| 2005/0113902 A1 | 5/2005 | Geiser et al. |
| 2005/0137681 A1 | 6/2005 | Shoemaker et al. |
| 2005/0165442 A1 | 7/2005 | Thinnes et al. |
| 2005/0192616 A1 | 9/2005 | Callister et al. |
| 2005/0209675 A1 | 9/2005 | Ton et al. |
| 2005/0288684 A1 | 12/2005 | Aronson et al. |
| 2006/0009798 A1 | 1/2006 | Callister et al. |
| 2006/0052822 A1 | 3/2006 | Mirizzi et al. |
| 2006/0119714 A1 | 6/2006 | Tamura et al. |
| 2006/0149359 A1 | 7/2006 | Richter et al. |
| 2006/0162731 A1 | 7/2006 | Wondka et al. |
| 2006/0178727 A1 | 8/2006 | Richter |
| 2006/0184089 A1 | 8/2006 | Makower et al. |
| 2006/0200191 A1 | 9/2006 | Zadno-Azizi |
| 2006/0241675 A1 | 10/2006 | Johnson et al. |
| 2006/0241690 A1 | 10/2006 | Amplatz et al. |
| 2007/0038178 A1 | 2/2007 | Kusleika |
| 2007/0043419 A1 | 2/2007 | Nikolchev et al. |
| 2007/0060946 A1 | 3/2007 | Keegan et al. |
| 2007/0088388 A1 | 4/2007 | Opolski et al. |
| 2007/0112381 A1 | 5/2007 | Figulla et al. |
| 2007/0118209 A1 | 5/2007 | Strecker |
| 2007/0129753 A1 | 6/2007 | Quinn et al. |
| 2007/0135826 A1 | 6/2007 | Zaver et al. |
| 2007/0150045 A1 | 6/2007 | Ferrera |
| 2007/0156224 A1 | 7/2007 | Cioanta et al. |
| 2007/0163601 A1 | 7/2007 | Pollock et al. |
| 2007/0168018 A1 | 7/2007 | Amplatz et al. |
| 2007/0168019 A1 | 7/2007 | Amplatz et al. |
| 2007/0203503 A1 | 8/2007 | Salahieh et al. |
| 2007/0221230 A1 | 9/2007 | Thompson et al. |
| 2007/0239191 A1 | 10/2007 | Ramzipoor |
| 2007/0247680 A1 | 10/2007 | Nakane et al. |
| 2007/0265656 A1 | 11/2007 | Amplatz et al. |
| 2007/0265658 A1 | 11/2007 | Nelson et al. |
| 2008/0017201 A1 | 1/2008 | Sawhney |
| 2008/0045996 A1 | 2/2008 | Makower et al. |
| 2008/0086214 A1 | 4/2008 | Hardin et al. |
| 2008/0103522 A1 | 5/2008 | Steingisser et al. |
| 2008/0132906 A1 | 6/2008 | Rasmussen |
| 2008/0178890 A1 | 7/2008 | Townsend et al. |
| 2008/0200945 A1 | 8/2008 | Amplatz et al. |
| 2008/0215087 A1 | 9/2008 | Pavcnik et al. |
| 2008/0221600 A1 | 9/2008 | Dieck et al. |
| 2008/0269719 A1 | 10/2008 | Balgobin et al. |
| 2008/0302368 A1 | 12/2008 | McGuckin, Jr. et al. |
| 2009/0005847 A1 | 1/2009 | Adams |
| 2009/0018562 A1 | 1/2009 | Amplatz et al. |
| 2009/0018636 A1 | 1/2009 | Gailloud et al. |
| 2009/0025820 A1 | 1/2009 | Adams |
| 2009/0030497 A1 | 1/2009 | Metcalf et al. |
| 2009/0043330 A1 | 2/2009 | To |
| 2009/0062841 A1 | 3/2009 | Amplatz et al. |
| 2009/0078270 A1 | 3/2009 | Meier et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0131959 A1 | 5/2009 | Rolland |
| 2009/0132020 A1 | 5/2009 | Watson |
| 2009/0138078 A1 | 5/2009 | Paul, Jr. et al. |
| 2009/0157053 A1 | 6/2009 | Davis et al. |
| 2009/0171386 A1 | 7/2009 | Amplatz et al. |
| 2009/0178682 A1 | 7/2009 | Tal et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0216185 A1 | 8/2009 | Gregorich et al. |
| 2009/0240326 A1 | 9/2009 | Wilson et al. |
| 2009/0276029 A1 | 11/2009 | Caro et al. |
| 2009/0276039 A1 | 11/2009 | Meretei |
| 2009/0277455 A1 | 11/2009 | Lee-Sepsick et al. |
| 2009/0281610 A1 | 11/2009 | Parker |
| 2010/0006105 A1 | 1/2010 | Carter et al. |
| 2010/0030321 A1 | 2/2010 | Mach |
| 2010/0049307 A1 | 2/2010 | Ren |
| 2010/0057194 A1 | 3/2010 | Ryan |
| 2010/0063578 A1 | 3/2010 | Ren et al. |
| 2010/0063582 A1 | 3/2010 | Rudakov |
| 2010/0089406 A1 | 4/2010 | Kachiguina |
| 2010/0106235 A1 | 4/2010 | Kariniemi et al. |
| 2010/0114307 A1 | 5/2010 | Agnew et al. |

(56) References Cited

U.S. PATENT DOCUMENTS

| | | |
|---|---|---|
| 2010/0121370 A1 | 5/2010 | Kariniemi |
| 2010/0174269 A1 | 7/2010 | Tompkins et al. |
| 2010/0198328 A1* | 8/2010 | Hartley et al. ............... 623/1.11 |
| 2010/0223046 A1 | 9/2010 | Bucchieri et al. |
| 2010/0223048 A1 | 9/2010 | Lauder |
| 2010/0249691 A1 | 9/2010 | Van Der Mooren et al. |
| 2010/0268201 A1* | 10/2010 | Tieu et al. .......................... 606/1 |
| 2010/0268260 A1 | 10/2010 | Riina et al. |
| 2010/0294282 A1 | 11/2010 | Chu et al. |
| 2010/0312268 A1 | 12/2010 | Belson |
| 2010/0318178 A1 | 12/2010 | Rapaport et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0029067 A1 | 2/2011 | McGuckin, Jr. et al. |
| 2011/0040371 A1 | 2/2011 | Hanssen et al. |
| 2011/0124958 A1 | 5/2011 | Nelson |
| 2011/0125132 A1 | 5/2011 | Krolik et al. |
| 2011/0202087 A1 | 8/2011 | Vale |
| 2011/0202129 A1 | 8/2011 | Fofsell |
| 2011/0218479 A1 | 9/2011 | Rottenberg et al. |
| 2011/0264132 A1 | 10/2011 | Strauss et al. |
| 2011/0264195 A1 | 10/2011 | Griswold |
| 2011/0282343 A1 | 11/2011 | Kunis |
| 2011/0301630 A1 | 12/2011 | Hendriksen et al. |
| 2011/0313506 A1 | 12/2011 | Ray et al. |
| 2011/0319906 A1* | 12/2011 | Rudakov et al. ............... 606/127 |
| 2012/0010556 A1 | 1/2012 | Faul et al. |
| 2012/0022572 A1 | 1/2012 | Braun et al. |
| 2012/0083822 A1* | 4/2012 | Anukhin et al. ............... 606/200 |
| 2012/0089216 A1 | 4/2012 | Rapaport et al. |
| 2012/0095489 A1* | 4/2012 | Rudakov et al. ............... 606/191 |
| 2012/0101510 A1 | 4/2012 | Lenker et al. |
| 2012/0116350 A1 | 5/2012 | Strauss et al. |
| 2012/0123511 A1 | 5/2012 | Brown |
| 2012/0123514 A1 | 5/2012 | Kunis |
| 2012/0143301 A1 | 6/2012 | Maslanka et al. |
| 2012/0172911 A1 | 7/2012 | Welch |
| 2012/0192872 A1* | 8/2012 | Rudakov et al. ............... 128/831 |
| 2012/0209310 A1 | 8/2012 | Chen et al. |
| 2012/0239077 A1 | 9/2012 | Zaver et al. |
| 2012/0245620 A1 | 9/2012 | Gilson et al. |
| 2012/0245668 A1 | 9/2012 | Kariniemi et al. |
| 2012/0259354 A1 | 10/2012 | Kellett |
| 2012/0277842 A1* | 11/2012 | Kunis .......................... 623/1.11 |
| 2012/0289988 A1 | 11/2012 | Riina et al. |
| 2012/0289994 A1 | 11/2012 | Larson et al. |
| 2012/0316584 A1 | 12/2012 | Miles et al. |
| 2012/0330347 A1 | 12/2012 | Becking et al. |
| 2012/0330348 A1 | 12/2012 | Strauss et al. |
| 2013/0053879 A1 | 2/2013 | Gailloud et al. |
| 2013/0102996 A1 | 4/2013 | Strauss |
| 2013/0103074 A1 | 4/2013 | Riina et al. |
| 2013/0109987 A1 | 5/2013 | Kunis et al. |
| 2013/0116774 A1 | 5/2013 | Strauss et al. |
| 2013/0123899 A1 | 5/2013 | Leopold et al. |
| 2013/0178889 A1 | 7/2013 | Miles et al. |
| 2013/0204282 A1 | 8/2013 | Nelson |
| 2013/0204311 A1* | 8/2013 | Kunis .............................. 607/14 |
| 2013/0289714 A1 | 10/2013 | Strauss et al. |
| 2014/0128780 A1 | 5/2014 | Kennedy et al. |
| 2014/0215792 A1* | 8/2014 | Leopold et al. ................. 29/428 |
| 2014/0222059 A1* | 8/2014 | Leopold et al. ............... 606/200 |
| 2014/0257369 A1* | 9/2014 | Leopold et al. ............... 606/200 |

FOREIGN PATENT DOCUMENTS

| | | |
|---|---|---|
| EP | 1 188 413 | 3/2002 |
| EP | 1317908 A2 | 6/2003 |
| EP | 1600110 | 11/2005 |
| EP | 1707233 A2 | 10/2006 |
| EP | 1752112 | 2/2007 |
| EP | 1813196 | 8/2007 |
| EP | 1820436 A2 | 8/2007 |
| EP | 1852073 | 11/2007 |
| EP | 2248471 | 11/2010 |
| EP | 2366362 | 9/2011 |
| EP | 2366363 | 9/2011 |
| EP | 2366364 | 9/2011 |
| EP | 2404580 | 1/2012 |
| EP | 2583636 | 4/2013 |
| GB | 2404860 A | 2/2005 |
| GB | 2494820 A | 3/2013 |
| JP | H 07-000405 | 1/1995 |
| JP | 07-18501 | 7/1995 |
| JP | 2006-181015 A | 7/2006 |
| JP | 2010-532180 A | 10/2010 |
| JP | 2012-525859 A | 10/2012 |
| WO | WO-83/00997 | 3/1983 |
| WO | WO-92/14408 | 9/1992 |
| WO | WO-94/00179 A1 | 1/1994 |
| WO | WO-95/24158 | 9/1995 |
| WO | WO-95/25480 A1 | 9/1995 |
| WO | WO-95/32018 | 11/1995 |
| WO | WO-96/18361 | 6/1996 |
| WO | WO-97/13463 | 4/1997 |
| WO | WO-97/13471 | 4/1997 |
| WO | WO-97/27893 | 8/1997 |
| WO | WO-97/27897 | 8/1997 |
| WO | WO-97/27898 | 8/1997 |
| WO | WO-97/31672 | 9/1997 |
| WO | WO-98/08456 | 3/1998 |
| WO | WO-98/31308 | 7/1998 |
| WO | WO-98/34546 | 8/1998 |
| WO | WO-98/46115 A2 | 10/1998 |
| WO | WO-98/46119 | 10/1998 |
| WO | WO-99/12484 | 3/1999 |
| WO | WO-99/23976 | 5/1999 |
| WO | WO-99/25273 | 5/1999 |
| WO | WO-99/44542 A2 | 9/1999 |
| WO | WO-99/48545 | 9/1999 |
| WO | WO-99/49793 | 10/1999 |
| WO | WO-99/49910 A2 | 10/1999 |
| WO | WO-99/62430 | 12/1999 |
| WO | WO-00/09195 | 2/2000 |
| WO | WO-00/16847 | 3/2000 |
| WO | WO-00/27303 A2 | 5/2000 |
| WO | WO-00/67671 | 11/2000 |
| WO | WO-01/32254 | 5/2001 |
| WO | WO-01/64112 A1 | 9/2001 |
| WO | WO-01/80776 | 11/2001 |
| WO | WO-01/80777 A2 | 11/2001 |
| WO | WO-01/89413 A2 | 11/2001 |
| WO | WO-02/03889 | 1/2002 |
| WO | WO-03/001970 A2 | 1/2003 |
| WO | WO-03/073961 | 9/2003 |
| WO | WO-03/073962 | 9/2003 |
| WO | WO-03/101518 | 12/2003 |
| WO | WO-2004/006804 | 1/2004 |
| WO | WO-2004/073557 A2 | 9/2004 |
| WO | WO-2005/020786 A2 | 3/2005 |
| WO | WO-2005/092241 | 10/2005 |
| WO | WO-2006/017470 A2 | 2/2006 |
| WO | WO-2006/028943 | 3/2006 |
| WO | WO-2006/031602 | 3/2006 |
| WO | WO-2006/034153 A2 | 3/2006 |
| WO | WO-2006/074163 A2 | 7/2006 |
| WO | WO-2006/096342 | 9/2006 |
| WO | WO-2006/111801 A2 | 10/2006 |
| WO | WO-2006/134354 | 12/2006 |
| WO | WO-2007/061927 A2 | 5/2007 |
| WO | WO-2007/070544 A2 | 6/2007 |
| WO | WO-2007/085373 | 8/2007 |
| WO | WO-2007/127351 | 11/2007 |
| WO | WO-2007/149844 A2 | 12/2007 |
| WO | WO-2008/010197 A2 | 1/2008 |
| WO | WO-2008/100790 A2 | 8/2008 |
| WO | WO-2008/112501 | 9/2008 |
| WO | WO-2008/153653 | 12/2008 |
| WO | WO-2009/064618 | 5/2009 |
| WO | WO-2009/077845 A2 | 6/2009 |
| WO | WO-2009/088905 | 7/2009 |

(56) References Cited

FOREIGN PATENT DOCUMENTS

| WO | WO-2009/124288 | 10/2009 |
|---|---|---|
| WO | WO-2009/126747 | 10/2009 |
| WO | WO-2010/009019 | 1/2010 |
| WO | WO-2010/047644 | 4/2010 |
| WO | WO-2010/075565 A2 | 7/2010 |
| WO | WO-2010/085344 A1 | 7/2010 |
| WO | WO-2010/096717 | 8/2010 |
| WO | WO-2010/130617 | 11/2010 |
| WO | WO-2010/135352 A1 | 11/2010 |
| WO | WO-2010/146581 | 12/2010 |
| WO | WO-2010/148246 A2 | 12/2010 |
| WO | WO-2011/011581 A2 | 1/2011 |
| WO | WO-2011/153304 | 12/2011 |
| WO | WO-2011/163157 A2 | 12/2011 |
| WO | WO-2012/002944 | 1/2012 |
| WO | WO-2012/040380 | 3/2012 |
| WO | WO-2012/067724 | 5/2012 |
| WO | WO-2012/109367 | 8/2012 |
| WO | WO-2012/111137 | 8/2012 |
| WO | WO-2012/120490 A2 | 9/2012 |
| WO | WO-2012/131672 A2 | 10/2012 |
| WO | WO-2012/134761 | 10/2012 |
| WO | WO-2012/135859 A2 | 10/2012 |
| WO | WO-2012/166804 | 12/2012 |
| WO | WO-2013/055703 A1 | 4/2013 |
| WO | WO-2013/059511 A1 | 4/2013 |
| WO | WO-2013/067299 | 5/2013 |

OTHER PUBLICATIONS

Berguer et al., Cure by Combination of Operation and Detachable Intravascular Balloon, Ann. Surg. Jul. 1982, pp. 65-68, vol. 196, No. 1.

Cheng et al., Minimally Invasive Keyhole Approach for Removal of a Migratory Balloon Complicated by Endovascular Embolization of a Carotid-Cavernous Fistula, Minim. Invasive Neurosurgl, 2006, pp. 305-308, vol. 49.

DeSouza et al., Embolization with detachable Balloons—Applications outside the head, Clinical Radiology, Apr. 21, 1992, pp. 170-175, vol. 46.

Ferro et al, Percutaneous Transcatheter Embolization of a Large Pulmonary Arteriovenous Fistula with an Amplatzer Vascular Plug, Cardovacs Intervent Radiol, 2007, pp. 328-331, vol. 30.

Hawkins et al., The Permeability of Detachable Latex Rubber Balloons—An In Vitro Study, Investigative Radiology, Dec. 1987, pp. 969-972, vol. 22.

Hirai et al., Emergency Balloon Embolization for Carotid Artery Rupture Secondary to Postoperative Infection, Cardiovasc Intervent Radiol, 1996, pp. 50-52, vol. 19.

Kadir et al., Therapeutic Embolization of the Kidney with Detachable Silicone Balloons, The Journal of Urology, Jan. 1983, pp. 11-13, vol. 129.

Kallmes et al., The Use of Hydrocoil for Parent Artery Occlusion, AJNR Am J Neuroradiol, Sep. 2004, pp. 1409-1410, vol. 25.

Kaufman, et al., Detachable Balloon-modified Reducing Stent to Treat Hepatic Insufficiency after Transjugular Intrahepatic Portosystemic Shunt Creation, J Vasc Interv Radiol., May 2003, pp. 635-638, vol. 14, No. 5.

Luo, Chao-Bao et al., Endovascular Treatment of the Carotid Artery Rupture with Massive Hemorrhage, J. Chin Med Assoc., Mar. 2003.

Makita, et al., Guide-Wire-directed Detachable Balloon: Clinical Application in Treatment of Varicoceles, Radiology, 1992, pp. 575-577, vol. 183.

Marshall et al., Treatment of Traumatic Renal Arteriovenous Fistulas by Detachable Silicone Balloon Embolization, The Journal of Urology, Aug. 1979, pp. 237-239, vol. 122.

Perala et al., Comparison of Early Deflation Rate of Detachable Latex and Silicone Balloons and Observations on Persistent Varicocele, J. Vasc. Interv. Radiol. Sep.-Oct. 1998, pp. 761-765, vol. 9, No. 5.

Pollak et al., Clinical Results of Transvenous Systemic Embolotherapy with a Neuroradiologic Detachable Balloon, Radiology, May 1994, pp. 477-482, vol. 191, No. 2.

Reidy et al., Transcatherer occlusion of coronary to bronchial anastomosis by detachable balloon combined with coronary angioplasty at same procedure, Brit Heart J. 1983, pp. 284-287, vol. 49.

Reidy et al., Transcatheter occlusion of a Blalock-Taussig shunt with a detachable balloon in a child, Bri Heart Journal, 1983, pp. 101-103, vol. 50.

Ross et al., The Vascular Plug: A New Device for Parent Artery Occlusion, AJNR Am J Neuroradiol, Feb. 2007, pp. 385-386, vol. 28.

Serbinenko, F.A., Balloon Catheterization and Occlusion of Major Cerebral Vessels, J. Neurosurg. Aug. 1974, pp. 125-145, vol. 41.

Tasar, et al., Intrahepatic arterioportal fistula and its treatment with detachable balloon and transcatheter embolization with coils and microspheres, Journal of Clinical Imaging, 2005, pp. 325-330, vol. 29.

Wehman, et al., Giant Cerebral Aneurysms: Endovascular Challenges, Neurosurgery, Nov. 2006, pp. S125-S138, vol. 59, No. 5.

White, et al., Occlusion of Varicoceles with Detachable Balloons, Radiology, May 1981, pp. 327-334, vol. 139.

Serbinenko, F.A., Occlusion by Balooning of Sacular Aneurysms of the Cerebral Arteries, Vopr, Neirokhir, Jul.-Aug. 1974, pp. 8-15, vol. 4.

Serebinko, F.A., Balloon Occlusion of Cavernous Portion of the Carotid Artery as a Method of Treating Carotid Cavity Anastomoses, Vopr. Neirokhir, Nov.-Dec. 1971, pp. 3-9, vol. 6.

U.S. Appl. No. 13/828,974, filed Mar. 14, 2013.

U.S. Appl. No. 14/044,794, filed Oct. 2, 2013.

U.S. Appl. No. 14/101,171, filed Dec. 9, 2013.

International Search Report and Written Opinion dated Apr. 25, 2014, which issued in International Application No. PCT/US2014/014889.

International Search Report and Written Opinion dated Jul. 8, 2014, which issued in International Application No. PCT/US2013/076964.

* cited by examiner

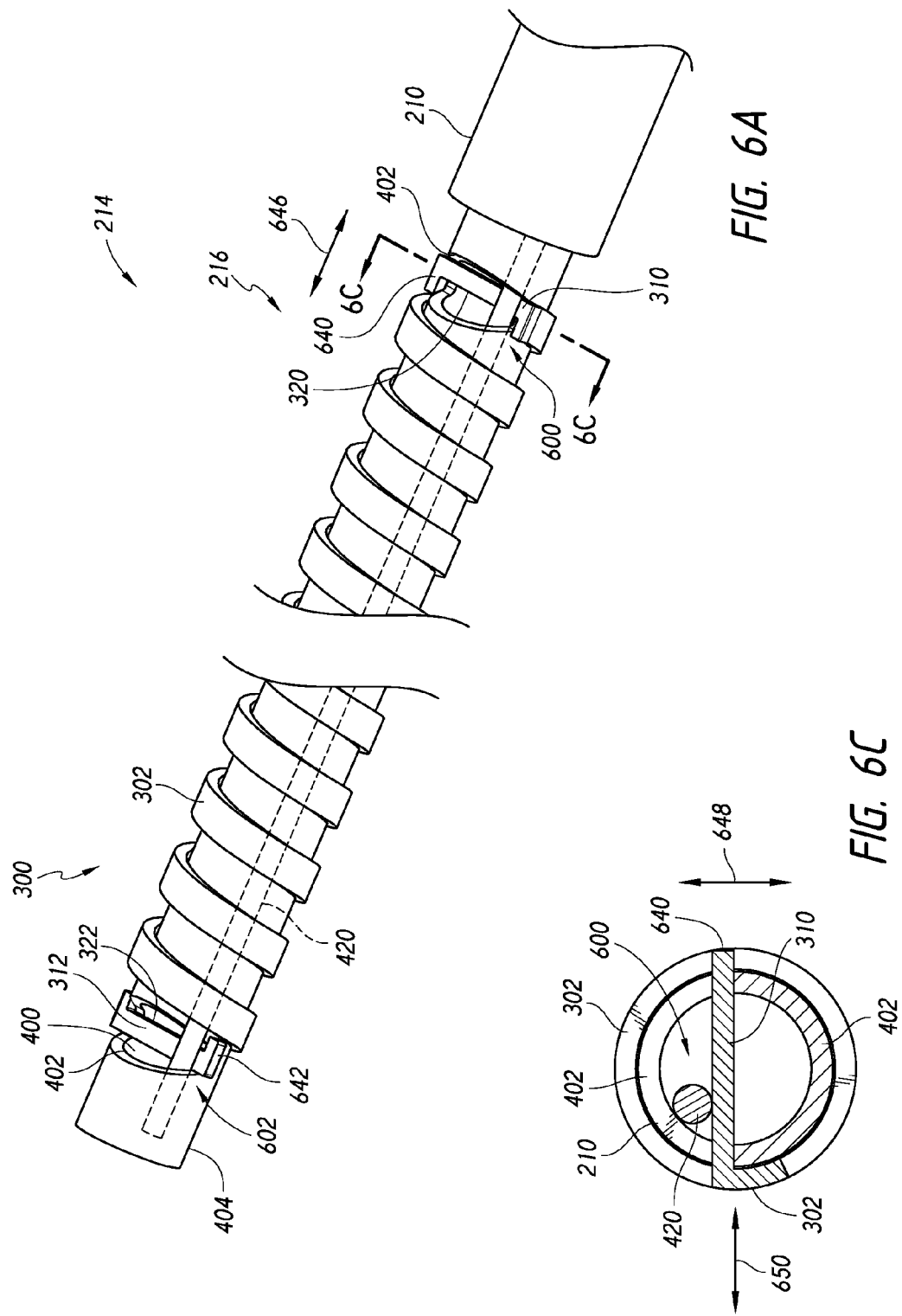

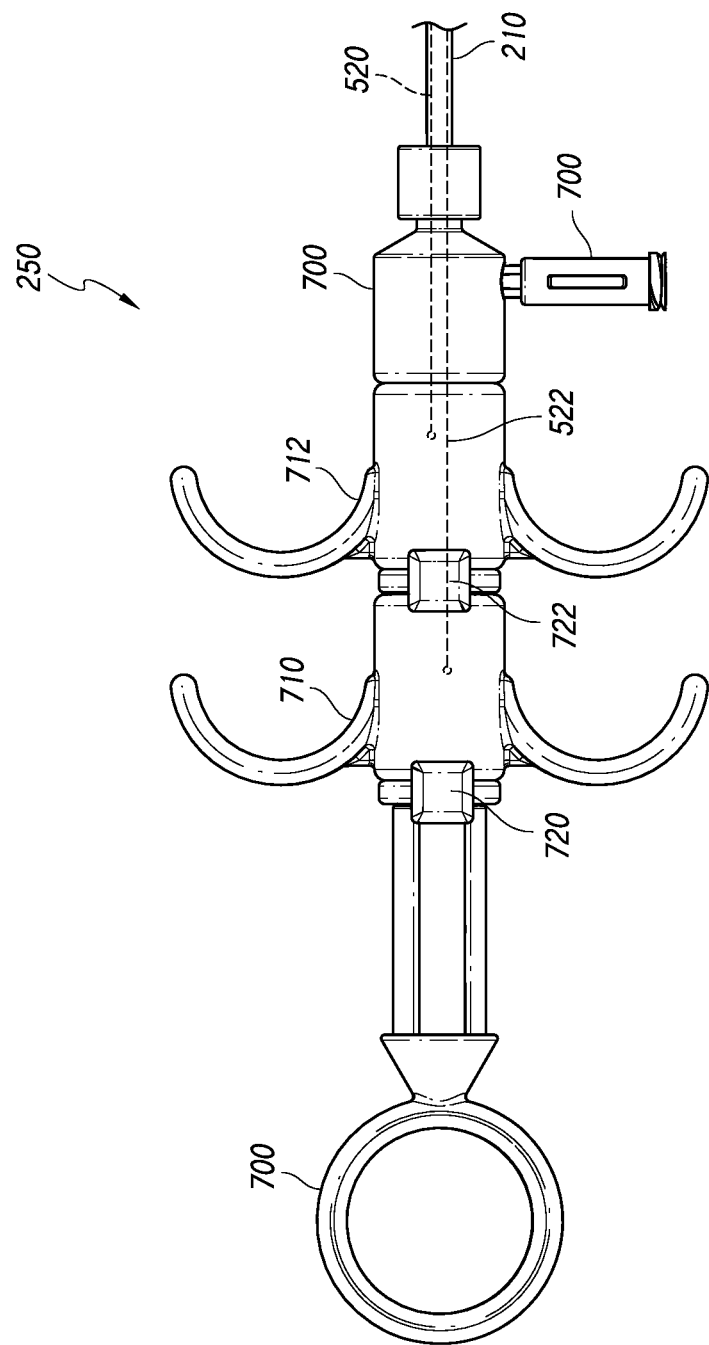

BLOOD VESSEL OCCLUSION

CROSS-REFERENCE TO RELATED APPLICATIONS

This application is a continuation of U.S. patent application Ser. No. 13/828,974, filed on Mar. 14, 2013, which claims the priority benefit of U.S. Provisional Application No. 61/761,195, filed on Feb. 5, 2013, the entirety of each of which is incorporated herein by reference.

BACKGROUND

1. Field of the Inventions

The subject technology relates generally to apparatuses and methods for blood vessel occlusion, e.g., endoluminal occlusion systems and their methods of use.

2. Description of the Related Art

Rapid, well-controlled, and safe methods to limit bleeding in vessels have encouraged the development of endovascular devices and techniques, and their introduction into clinical practice. Early devices used balloons, either non-detachable or later detachable, in order to block vessels, for example, in the treatment of carotid-cavernous fistulas and saccular aneurysms.

Typically made from latex or silicone, balloons are delivered to a desired location in a vessel, and then inflated in order to physically occlude the vessel. While other devices have since been developed, balloon occlusion remains in use, and is indicated for use in treating a variety of life-threatening conditions, including for example, giant cerebral and skull base aneurysms, traumatic and non-traumatic vessel injury or rupture, vertebro-vertebral arteriovenous fistulas, and preoperative tumor resections.

Detachable balloons are also useful clinically in procedures outside of neurological intervention. For example, balloons can be useful in flow reduction procedures such as shunt occlusion in patients with transjugular intrahepatic portosystemic shunts and hepatic insufficiency, intrahepatic arterioportal fistulas, treatment of varicoceles, shunt occlusion in patients with a Blalock-Taussig shunt, obliteration of pulmonary arteriovenous fistulas, arteriovenous malformations or aortopulmonary anastomoses, coronary arteriovenous fistulas, or renal arteriovenous fistulas. Detachable balloons are also used in preoperative devascularization before surgical resection of organs such as the kidney.

SUMMARY

Despite their usefulness, balloon occlusion devices suffer from limitations that affect their ease of use and safety. By its very nature, a balloon can expand and rupture, or alternatively it can spontaneously deflate over time. Deflation is more common with latex balloons, with some studies reporting 100% deflation rates. Spontaneous deflation can result in treatment failure and reoccurrence of the lesion.

Detachable balloon devices present other problems as well, and their use in the intracranial vasculature presents specific challenges. For example, balloons lack trackability, meaning that they are difficult to navigate, especially through tortuous vessels, such as those commonly found in the intracranial circulation. In addition, premature (i.e., non-intentional) detachment from the delivery device can lead to adverse consequences such as cerebral artery blockage and stroke.

Even once in place they typically move forward during the process of inflation, making placement of the unexpanded balloon in order to achieve precise positioning after inflation relatively difficult. Balloons that dislodge and migrate can require open skull surgery especially where the balloon has become lodged in a major vessel, for example, in a cerebral artery.

More recently, detachable balloons have become unavailable for use in the United States. Further, silicone balloons were retired from the market several years ago, and the only alternative, the Goldvalve™ latex balloon, is difficult to obtain, and its use carries the risk of adverse reaction in patients allergic to latex. Thus, a vacuum exists in the field of vessel occlusion therapies, and consequently, interventionalists are left with few options to perform vessel occlusion procedures.

One approach has been to use hydrogel-coated coils in order to produce rapid vascular occlusion. However, there still remains a significant period of time between placement of the coil, and formation of the occlusive clot, even when using coated coils. This leads to concern that during formation of the clot, distal clot migration can occur, with potentially devastating consequences such as stroke. Further, the geometric configuration and unpredictability of coil-based embolization prevents precise occlusion of a short vascular segment. The risk of distal migration of a clot is also of concern when treating high-flow peripheral lesions such as pulmonary arteriovenous fistulas.

The Amplatzer® Vascular Plug, a device made of a self-expanding Nitinol mesh, can be used to block flow through a vessel by inducing formation of a clot. However, as discussed above, this device is unable to provide for acute occlusion therapy and thus the risk of distal clot migration into remains. The device is also limited by it navigability, and placement precision, which limits its utility to use in performing occlusions below the base of the skull.

As a result of the limitations in prior art apparatus and methods for occluding vessels, the present disclosure recognizes that it is desirable to provide an apparatus and method that effectively provides acute blockage of a desired vessel, or alternatively, limited flow through a vessel, is relatively easy to place and deploy, and which will be stable over time, while avoiding limitations and problems inherent in the prior art apparatus and methods.

Accordingly, many conditions, including pelvic venous incompetence, create the need to close blood vessels that have lost their integrity. There a number of treatments aimed at closing these dilated veins, but even the most highly recommended procedure, microcoil embolization, involves deploying a large amount of permanent metallic coils within the body, as shown in FIG. 1. In this procedure, a coil 10 is inserted into a luminal space 20 in order to reduce or block flow through the luminal space 20. Generally, this procedure also involves exposure, and often prolonged exposure, to x-ray radiation 30. This can be harmful to patients, especially those of childbearing age.

Embodiments of the systems and devices disclosed herein address the unmet need for a device that can provide a fast, precise and reliable way to close a bodily lumen. The endoluminal occlusion system can include two major subsystems: a guide sheath assembly and an implant carrier assembly. The implant carrier assembly can include an implant device and a handle assembly. Embodiments of the present disclosure can also comprise various features disclosed in U.S. Pat. No. 8,328,840, issued on Dec. 11, 2012, entirety of which is incorporated herein by reference.

In accordance with some embodiments, a guide sheath assembly can be provided that comprises a guide sheath and a removable core. The guide sheath and the removable core can be advanced into a bodily lumen or vessel until reaching a target region. The guide sheath can have a lumen that is configured to receive the removable core therein. The removable core can also have a lumen that is configured to receive a guide wire therethrough. Thus, the removable core and the guide sheath can be advanced over the guide wire until reaching the target region of the bodily lumen or vessel. Once the guide sheath assembly is in place at the target region, the removable core can be removed, along with the guide wire, from the bodily lumen or vessel. At this stage, the guide sheath can remain placed at the target region.

The implant carrier assembly can be configured to be inserted into the lumen of the guide sheath. The implant carrier assembly can comprise a catheter that is attached to the handle assembly at a proximal end of the catheter. The catheter can also define a distal end that is configured to support the implant thereon.

The handle assembly can comprise one or more actuator members that can be actuated to selectively release or disengage at least a portion of the implant from the distal end of the catheter. In some embodiments, the actuator member(s) can comprise a slider or pull member.

The slider or pull member can be coupled to a handle frame component. The handle frame component can be coupled to the catheter and provide a generally fixed spatial relationship relative to the distal end of the catheter and the handle frame component. Thus, according to some embodiments, the slider or pull member can move relative to the distal end of the catheter.

In some embodiments, the slider or pull member can be coupled to an elongate wire that extends from the slider or pull member to the distal end of the catheter. Accordingly, when the slider or pull member is proximally retracted, a proximal retracting force is exerted upon the wire, which can result in disengagement of the implant from the distal end of the catheter. The elongate wire can have a diameter of from about 0.006 inches to about 0.008 inches. The presence of wires in the catheter can advantageously provide column strength for the implant carrier assembly.

In some embodiments, the handle assembly can comprise two or more actuator members, such as sliders or pull members. Further, the handle assembly can also comprise wires coupled to the sliders or pull members. The sliders or pull members can be coupled to the elongate wires that extend within a lumen of the catheter. For example, the handle assembly can have two actuator members and two wires.

The distal end of the catheter can comprise an engagement seat that is configured to receive and facilitate engagement with at least a portion of the implant to maintain the implant engaged with the distal end of the catheter.

The engagement seat can be configured to facilitate engagement between the implant and a wire extending from the handle assembly. In some embodiments, the engagement seat can facilitate engagement between the implant and two or more wires extending from the handle assembly.

In some embodiments, the engagement seat can comprise a generally tubular member having a lumen and at least one aperture or notch. At least a portion of the implant can be received into the aperture and be engaged with a member, such as an elongate member or wire, extending through the engagement seat lumen. For example, the implant can be disposed on the engagement seat, such as by being wound about the engagement seat.

In some embodiments, a flattened portion of the implant extending across the aperture within the catheter lumen. A wire can lock the flattened portion radially within the notch to prevent movement between the implant and the engagement seat.

In some embodiments, the flatten portion of the implant can comprise a notch. The notch can be received within the aperture of the engagement seat. Thus, when the elongate member is positioned so as to lock the flatten portion radially within the notch, the notch of the flattened portion can secure the flatten portion relative to the notch of the engagement seat to prevent the flattened portion from sliding out of the engagement seat notch.

The handle assembly can also comprise a fluid inlet for providing fluid to the distal end of the catheter. The distal end of the catheter can comprise one or more apertures or perforations for permitting the passage of fluid into the implant for flushing the device.

In use, in accordance with some embodiments, once guided to the vascular area to be closed, the sheath can be adjusted precisely to obtain optimal position within the vessel. The removable core and guide wire can then be taken out of the guiding sheath, and the implant carrier is advanced through the sheath. The proximal end of the device is released first, followed by the distal end. The device's membrane can be filled with incoming blood, helping the device to be secured against the vessel wall.

In order to release the device, according to some embodiments, the operator can remove the first clip from the handle assembly and then pulls the proximal slider to release the proximal end of the device. The second clip can then be removed from the handle assembly and the distal slider can be pulled to release the distal end of the device.

For example, in some embodiments, an occlusion device delivery system is provided that can comprise a catheter, and expandable coiled implant, and an elongate member. The catheter can have a lumen extending between distal and proximal portions. The distal portion can have proximal and distal apertures extending through a wall of the catheter. The expandable coiled implant can be wound about the distal portion. Further, the implant can have a proximal section that extends within the proximal aperture and a distal section that extends radially within the distal aperture. The elongate member can extend through the catheter lumen and engaging and radially restrain the at least one of the proximal or distal sections within its respective aperture while engaged with the member.

In some embodiments, the implant, when coiled about the distal portion, can comprise a lumen and at least one of the proximal or distal sections can extend across the implant lumen. Further, when the implant is coiled about the distal portion in some embodiments, the implant can extend between the proximal and distal apertures along a generally helical path and at least one of the proximal or distal sections can then radially inwardly from the helical path.

An occlusion implant or device can also be provided in some embodiments. The occlusion implant can comprise a helical member or wire supporting a generally impermeable membrane. The occlusion implant can have proximal and distal sections. The device proximal end section be open and the distal section can be closed to prevent passage of fluid through the implant. The implant can comprise any of the various features discussed herein.

The proximal and distal sections can extend across the catheter lumen. The proximal and distal sections can extend across the catheter lumen less than a diameter of the catheter lumen.

In some embodiments, the elongate member can extend through the catheter lumen and between at least one of the proximal or distal sections its respective aperture. Upon proximal withdrawal of the elongate member through the catheter lumen, the elongate member can be configured to disengage and radially release the at least one of the proximal or distal sections from its respective aperture. Further, in some embodiments, the elongate member can engage both the proximal and distal sections. The elongate member can comprise a wire.

In some embodiments, the at least one of the proximal or distal sections can have a respective end that is configured to extend radially out of its respective aperture while engaged with the member. Further, the respective end can be larger than the respective section extending through the aperture. Thus, the respective end and the respective section can engage the respective aperture such that the respective section is generally restrained from movement transverse to an axis of the catheter when the elongate member is engaged with and radially restrains the respective section within the respective aperture.

For example, the proximal section can be configured to comprise a reduced cross-sectional segment that is configured to extend within the proximal aperture. The reduced cross-sectional segment can be configured to extend within the distal aperture while the implant is coiled about the distal portion. Further, the reduced cross-sectional segment can comprise a notch. For example, in some embodiments, the notch and the aperture can each have substantially equal lengths, transverse to an axis of the catheter lumen. Further, the apertures can comprise slots that are transverse to an axis of the catheter lumen.

A handle assembly can also be provided for selectively releasing an intravascular implant device, the handle assembly having first and second sliders and first and second clips. The first and second clips can prevent movement of the first and second sliders and being removable from the handle assembly to permit movement of the first and second sliders. The first slider can be operative to disengage an implant device proximal end from the catheter. The second slider can be operative to disengage an implant device distal end from the catheter.

In some embodiments, a method of deploying an occlusion device in a blood vessel is provided. The method can comprise the steps of: advancing a catheter in a blood vessel to position an expandable coiled implant, wound about a distal portion of the catheter, the distal portion having proximal and distal apertures extending through a wall of the catheter, the implant having a proximal section that extends within the proximal aperture and a distal section that extends within the distal aperture; and proximally withdrawing an elongate member extending through a lumen of the catheter to proximally withdraw the elongate member through the catheter lumen.

The method can be implemented to further comprise the steps of: removing a first clip from a handle assembly to permit movement of a first slider of the handle assembly to proximally withdraw the elongate member; and proximally retracting the first slider to disengage and radially release the at least one of the implant proximal or distal sections from its respective aperture.

Further, the implant proximal section can be engaged and radially restrained by the elongate member, and the implant distal section can be engaged and radially restrained by a second elongate member extending through the catheter lumen. In some embodiments, the method can further comprise proximally withdrawing the second elongate member to disengage and radially release the implant distal section from its respective aperture.

The method can also comprise positioning a guide sheath at a treatment site and unsheathing an occlusion implant from the guide sheath. The implant can have proximal and distal sections that are engaged with a catheter. The catheter can be operatively interconnected with a handle assembly for selectively controlling engagement and release of the implant with the catheter.

The method can also be implemented to comprise the steps of: removing a second clip from the handle assembly to permit movement of a second slider of the handle assembly; and proximally retracting the second slider to proximally withdraw the second elongate member. The steps of removing a second clip and proximally retracting the second slider can be performed after the first slider has been proximally retracted. The method can also be implemented such that the steps of removing a second clip and proximally retracting the second slider are performed after the first slider has been proximally retracted.

Some embodiments can also provide an occlusion device delivery system that comprises a microcatheter, a removable core, and an implant assembly. The removable core can extend along an inner lumen of the microcatheter. The implant assembly can comprise a catheter, an occlusion device, and a handle assembly. The catheter can have a proximal end and a distal end. The occlusion device can be coupled to the catheter distal end. The occlusion device can have a helical wire supporting a generally impermeable membrane. The occlusion device can have proximal and distal ends. The handle assembly can have first and second sliders and first and second clips. The first and second clips can prevent movement of the first and second sliders and can be removable from the handle assembly to permit movement of the first and second sliders. The first slider can be operative to disengage the device proximal end from the catheter. The second slider can be operative to disengage the device distal end from the catheter.

In some embodiments, the system can be configured such that the catheter comprises first and second notches. Further, the helical wire of the occlusion device can comprise first and second portions that fit into the first and second notches.

The handle assembly can further comprise first and second wires coupled to the first and second sliders. The first and second wires can extend distally to engage with the first and second portions of the occlusion device to radially restrain the first and second portions of the occlusion device in the respective first and second notches.

Embodiments of the present system have the ability to close a bodily lumen or vessel rapidly and with confidence. This can provide improved health and quality of life for millions of people.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIGS. 6A-6D illustrate aspects of an implant scaffold on a catheter distal section of an implant carrier assembly, according to some embodiments.

FIG. 8 is a top view of a handle assembly, according to some embodiments.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

While the present description sets forth specific details of various embodiments, it will be appreciated that the description is illustrative only and should not be construed in any way as limiting. It is contemplated that although particular embodiments of the present inventions may be disclosed or shown in particular contexts, such embodiments can be used in a variety of endoluminal applications. Various applications of such embodiments and modifications thereto, which may occur to those who are skilled in the art, are also encompassed by the general concepts described herein.

According to some embodiments, the systems and methods disclosed herein can be used for percutaneous, peripheral occlusion of the peripheral arterial and venous vasculature. For example, some embodiments can be used to treat pelvic venous incompetence, varicocele, gonadal vein for pelvic varices in females with chronic pelvic pain, stop blood loss from a damaged blood vessel due to a traumatic arterial injury, stop hemorrhage caused by a neoplasia, and close an abnormal blood vessel or blood vessels supplying a vascular anomaly such as arteriovenous malformations or arteriovenous fistulas, and other conditions. Other uses and applications of the system are provided in the appended documents.

Figure 1:
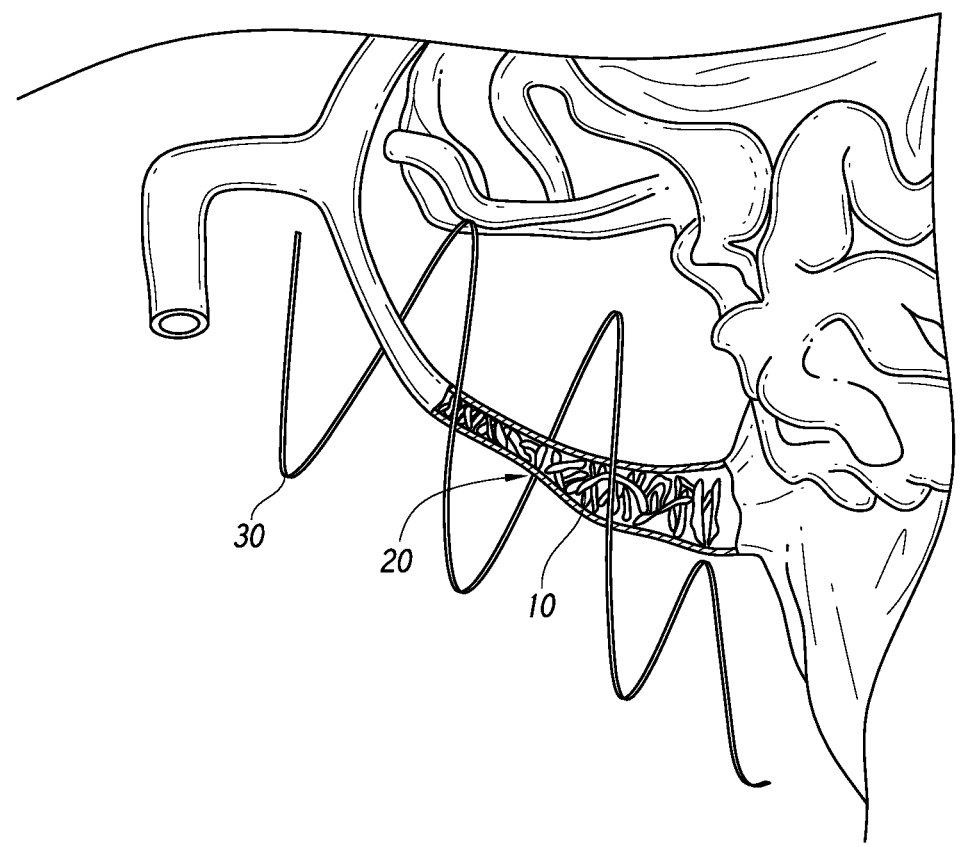
FIG. 1 is a schematic view of a body lumen having an occlusive coil disposed therein for treating pelvic venous incompetence.
Figure 2:
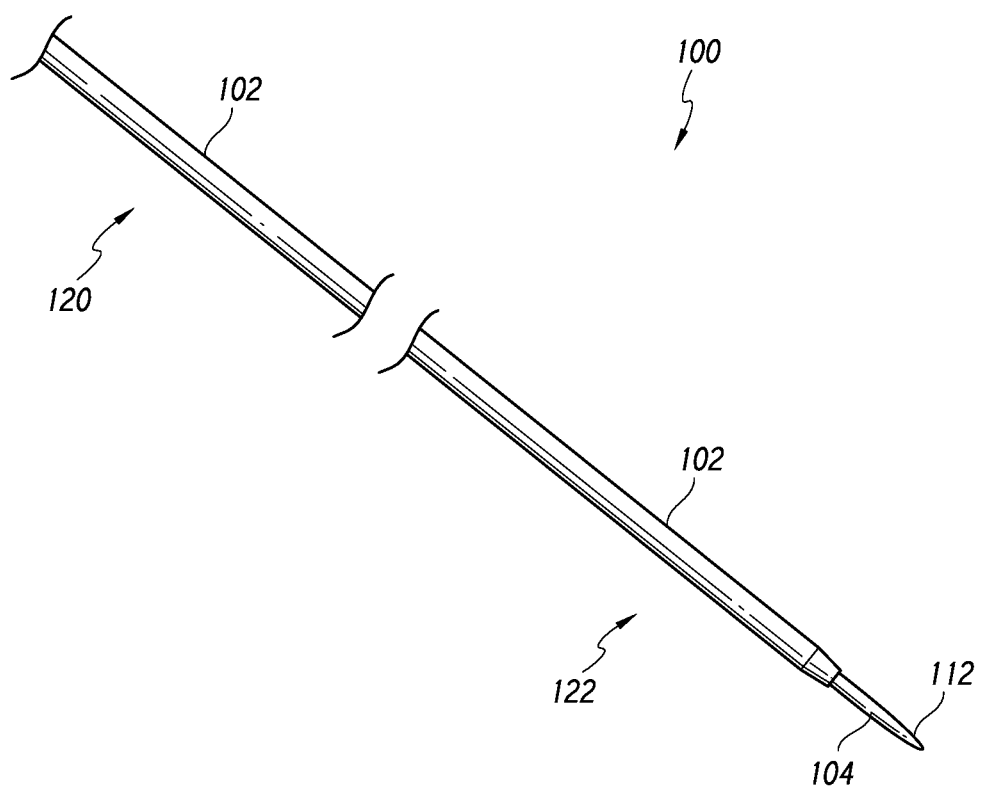
FIG. 2 is a top view of a guide sheath assembly, according to some embodiments.

Some embodiments comprise a guide sheath assembly that can be used to access a treatment site. The guide sheath assembly can be advanced to the treatment site, to deploy one or more devices, is disclosed herein. For example, FIG. 2 illustrates a guide sheath assembly 100 that comprises a guide sheath 102 and a removable core 104. In some embodiments, the guide sheath assembly 100 can be advanced over a wire to the treatment site. However, the guide sheath assembly 100 can also be configured to be advanced independently or without a wire.

The guide sheath assembly 100 can be configured such that the removable core 104 can fit inside a lumen of the guide sheath 102 and extend out of a distal end 110 of the sheath 102. The removable core 104 can comprise a distal tip 112 that can be configured to be atraumatic. For example, the distal tip 112 can be rounded (for example, in embodiments that are advanced over a wire) and/or comprise an atraumatic tip coil (for example, in embodiments that are advanced independently or without a wire).

The guide sheath 102 can comprise a braided shaft with a stiff proximal section 120 and a more flexible distal section 122 to enable tracking through tortuous peripheral vasculature. The guide sheath distal end 110 can be tapered and include a radiopaque marker that is visible under fluoroscopy.

In accordance with some embodiments, the total length of the guide sheath 102 can have a total length from about 40 cm to about 150 cm, from about 60 cm to about 120 cm, or from about 70 cm to about 90 cm. For example, in some embodiments, the total length of the guide sheath 102 can have a total length of about 80 cm. Further, some embodiments, the guide sheath 102 can have a working length from about 65 cm to about 110 cm, from about 75 cm to about 100 cm, or in some embodiments, about 89 cm.

Additionally, in some embodiments, the removable core can 104 have a lumen (not shown) through which a guidewire can extend and a tapered end 112 for ease of advancement into and through the blood vessel. The total length of the removable core 104 can be from about 50 cm to about 180 cm, from about 70 cm to about 150 cm, or in some embodiments, about 110 cm, with a working length of from about 85 cm to about 130 cm, from about 95 cm to about 120 cm, or in some embodiments, about 108 cm.

In order to place the guide sheath assembly 100 in a vessel of the body, a guide wire (having a diameter of 0.035") can be placed into the vessel, and the guide sheath 102 and removable core 104 can be advanced over the guide wire. The guide wire and removable core 104 can then be removed from the guide sheath 102 once the guide sheath 102 is in position for delivery of the implant.

After the guide sheath 102 is placed, an implant carrier assembly can be inserted into the guide sheath 102 and advanced to the treatment site.

Figure 3:
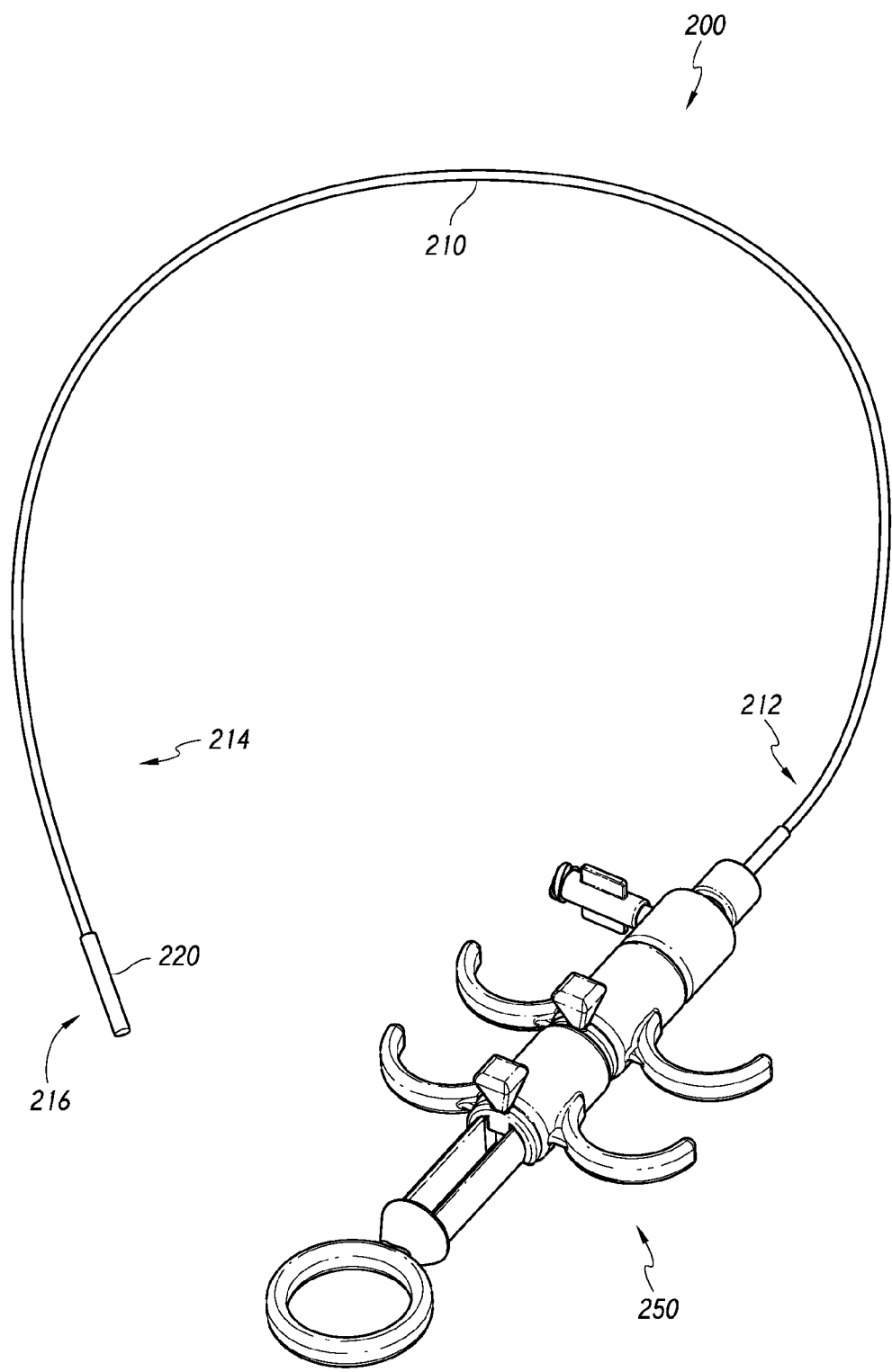
FIG. 3 is a perspective view of an implant carrier assembly, according to some embodiments.

FIG. 3 illustrates an embodiment of an implant carrier assembly 200 can comprise a catheter 210 having a lumen that extends between a proximal portion 212 and a distal portion 214 of the catheter. The catheter 210 can also comprise a distal engagement section 216 configured to engage and/or restrain an implant position thereabout. The catheter 210 can define a length from about 50 cm to about 200 cm, from about 70 cm to about 160 cm, or in some embodiments, about 120 cm, with a working length of from about 85 cm to about 140 cm, from about 95 cm to about 130 cm. In accordance with some embodiments, the total length of the implant carrier assembly (with handle) can be about 117 cm, with a working length of 97 cm.

The assembly 200 can also comprise an implant 220 loaded on the engagement section 216. Further, the assembly 200 can also comprise a deployment handle assembly 250 attached to the catheter proximal portion 212.

As noted above, the catheter 210 can be configured to within the guide sheath 102. The proximal portion 212 of the catheter 210 can have be configured to be relatively stiff in order to enhance the pushability of the catheter 210 through the guide sheath 102. Further, the distal portion 214 can be relatively flexible in order to improve the maneuverability and trackability of the catheter 210 as it is advanced through the guide sheath 102.

Figure 4:
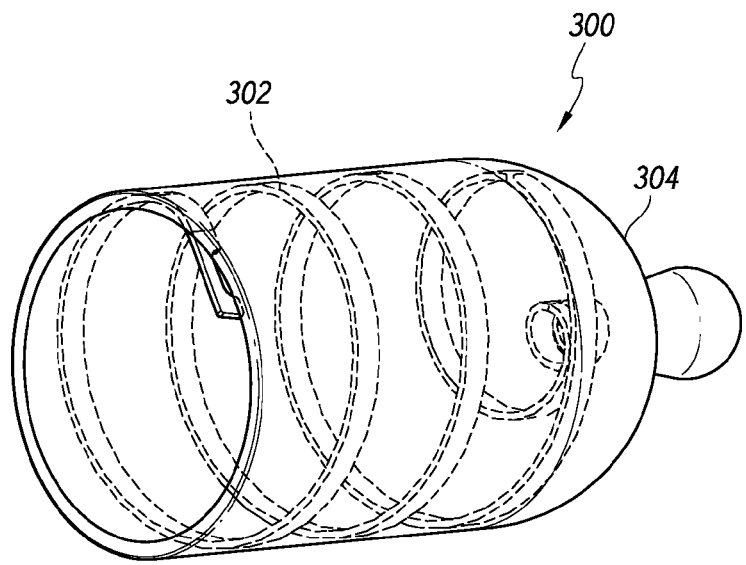
FIG. 4 is a perspective view of an implant, according to some embodiments.
Figure 5:
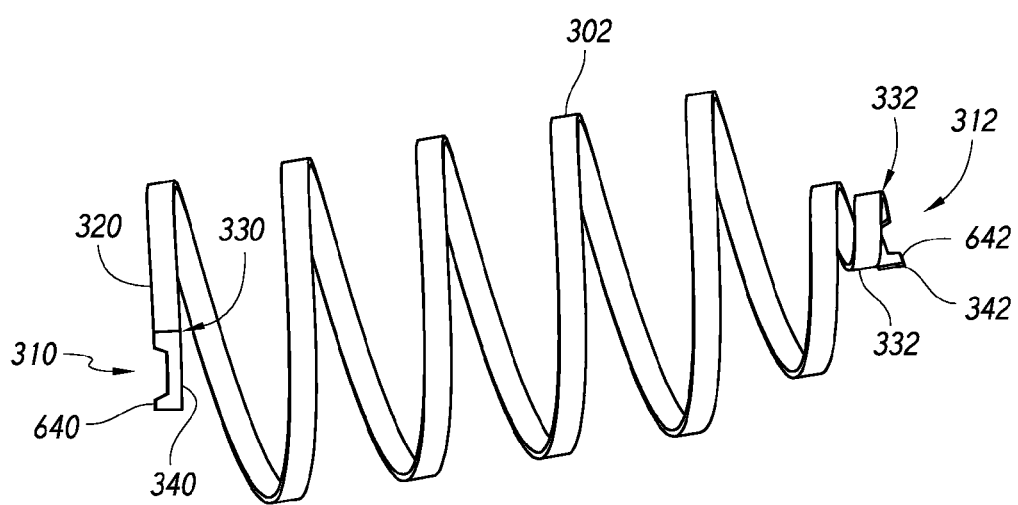
FIG. 5 is a perspective view of a scaffold of an implant, according to some embodiments.

Referring now to FIGS. 4-5, features of an embodiment of an implant 300 are illustrated. The implant 300 can comprise a scaffold 302 and a membrane 304 supported by the scaffold 302. The scaffold 302 can be formed from a variety of materials, which can be flexible or deformable. For example, the scaffold 302 can comprise nitinol. Additionally, the membrane 304 can comprise one or more of a variety of materials that can be impermeable or have low permeability. In some embodiments, the membrane 304 can be configured to occlude blood flow. For example, the membrane 304 can comprise polytetrafluoroethylene (PTFE), and similar materials, such as expanded polytetrafluoroethylene (ePTFE).

When implanted into a vessel, the implant 300 can be configured to provide sufficient radial strength against a vessel wall under normal blood pressure in order to minimize post-deployment migration.

The implant 300 can be configured with an expanded diameter depending on the target vessel size. For example, the implant 300 can have an expanded diameter of about 6 mm for vessels from about 3.0 mm to about 4.8 mm in diameter. Further, the implant can have an expanded diameter of about 9 mm for vessels from about 4.5 mm to to about 7.8 mm in diameter. Additionally, such embodiments can be compatible with, for example, a 6fr guiding catheter.

Referring now to FIG. 5, in some embodiments, the implant scaffold 302 can be formed as a helical body. For example, the scaffold 302 can define proximal and distal sections 310, 312. Generally, the body of the scaffold 302 can extend along a curvilinear, helical path. However, in accordance with some embodiments, one or both of the proximal or distal sections 310, 312 can bend radially inwardly from the helical path. In some embodiments, one or both of the proximal or distal sections 310, 312 can be configured to extend across the lumen of the scaffold 302, and/or across the lumen of the catheter 210, as discussed further below.

For example, the proximal section 310 can be configured to include an elbow 330 that causes a portion of the proximal section 310 to diverge from the generally helical path of the scaffold 302. The elbow 330 can comprise a change to a smaller radius of curvature compared to the radius of curvature of the helical path. Further, in some embodiments, the elbow 330 can define a generally right angle orientation for the proximal section 310.

Additionally, in some embodiments, the distal section 312 can also comprise an elbow 332. The elbow 332 can be configured similarly to the elbow 330 and allow a divergence in the path of the scaffold 304 at the distal section 312 thereof.

Further, in some embodiments, one or both of the proximal or distal sections 310, 312 can comprise a generally planar portion. For example, the proximal section 310 can comprise a planar portion 340 that extends from the elbow 330. The planar portion 340 can comprise a portion of the proximal section 310 that diverges from the helical path and extends generally within a plane. Thus, the planar portion 340 can be referred to as a flat or flattened portion that can extend in a generally linear or curvilinear direction within a plane. In some embodiments, the distal section 312 can also comprise a planar portion, which is illustrated in FIG. 5 as planar portion 342.

The planar portions 340, 342, whether either or both of them are included in an embodiment, can extend or bend radially inwardly from the helical path of the scaffold 302. Similarly, one or both of the planar portions 340, 342 can be configured to extend across the lumen of the scaffold 302, and/or across the lumen of the catheter 210, as discussed further below.

The scaffold 302 can comprise one or more reduced cross-sectional segments 320, 322. The segments 320, 322 can be disposed at the proximal section 310 and/or the distal section 312 of the scaffold 302. For example, FIG. 5 illustrates that the proximal section 310 comprises the reduced cross-sectional segment 320 and the proximal section 312 comprises a reduced cross-sectional segment 322.

In the illustrated embodiment, the reduced cross-sectional segments 320, 322 can comprise notches in the body of the scaffold 302. For example, the scaffold 302 can comprise a generally rectangular cross section and extend helically about a central axis or lumen, as illustrated in FIG. 5. The reduced cross-sectional segments 320, 322 can be indentations, protrusions, slots, and/or apertures extending through the scaffold 302. As discussed further below, the segments 320, 322 can be configured to interact with respective structures of the engagement section 216 of the catheter 210.

Figure 6B:
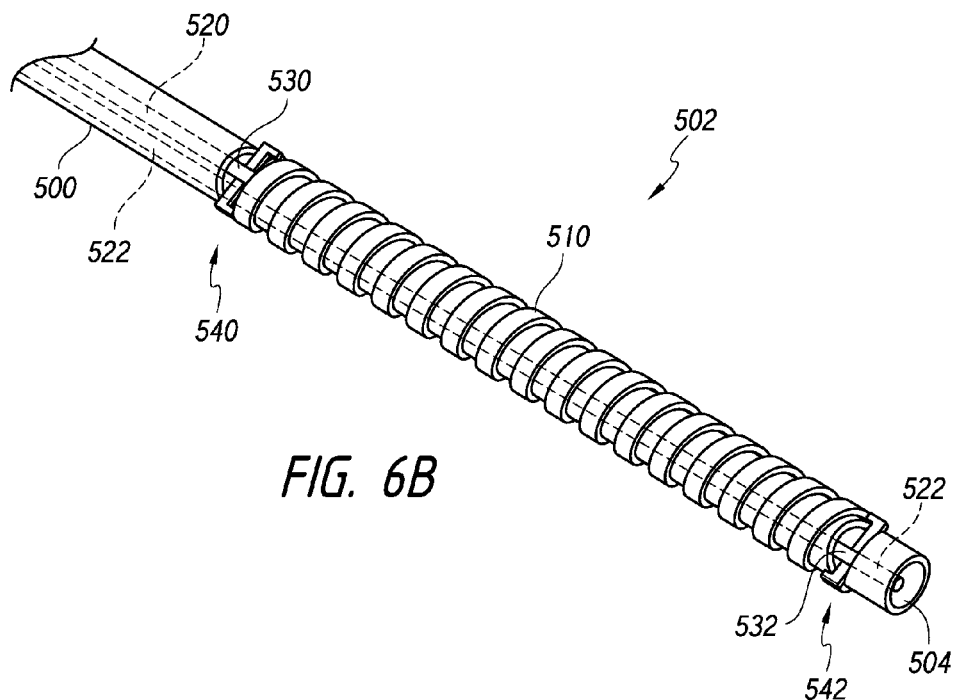

For example, FIGS. 6A-6C illustrate some embodiments of implant carrier assemblies. FIG. 6A illustrates an enlarged view of a distal engagement section or seat 216 located at a distal portion 214 of the catheter 210. The catheter 210 can comprise a lumen 400 extending through the catheter 210 and a catheter wall 402 formed between the catheter lumen 400 and an exterior surface 404 of the catheter 210.

As shown in FIG. 6A, the distal engagement section 216 can be configured to receive and facilitate engagement with at least a portion of an implant (illustrated only as scaffold 302, but which can include a membrane, as discussed above) to maintain the implant engaged with the distal end 214 of the catheter 210.

In accordance with some embodiments, the implant carrier assembly 200 can also be configured to comprise at least one elongate member 420 that extends at least partially through the catheter lumen 400. The elongate member 420 can engage at least a portion of, and in some embodiments, one or both the proximal and distal sections 310, 312, of the scaffold 302. The elongate member 420 can comprise a wire. However, in some embodiments, the elongate member 420 can comprise a plug or other structure that can interact with one or both of the proximal or distal sections 310, 312 of the implant 300.

In some embodiments, the elongate member 420 can be actuatable or controllable using the handle assembly 250, as discussed further below.

For example, the engagement section 216 can be configured to facilitate engagement between the scaffold 302 and the elongate member 420 extending from the handle assembly. In some embodiments, the elongate member 420 can be selectively actuated or withdrawn in order to release engagement between the scaffold 302 in the elongate member 420. The movement of the elongate member 420 can be configured to be a proximal withdrawal of the elongate member 420. However, the elongate member 420 can also be configured such that disengagement occurs when the elongate member is distally advanced (such as when a proximally oriented hook or segment of the elongate member 420 engages with the scaffold 302). Indeed, the elongate member 420 can be moved a first distance (whether proximally or distally) in order to release or disengage with one of the proximal or distal sections 310, 312 of the scaffold 302. Further, the elongate member can be moved a second distance, greater than the first distance (whether proximally or distally) in order to release or disengage with the other one of the proximal or distal sections 310, 312 of the scaffold 302.

Further, in some embodiments, the engagement section 216 can facilitate engagement between the implant 300 and two or more elongate members 420 extending from the handle assembly 250. Although the elongate member 420 is illustrated as extending between the proximal and distal sections 310, 312 of the implant scaffold 302, the elongate member 420 can engage one of the proximal or distal sections 310, 312 while a second elongate member can be used to engage the other of the proximal or distal sections 310, 312.

For example, FIG. 6B illustrates an embodiment of an implant assembly in which a catheter 500 comprises an engagement section 502 and a lumen 504. The assembly can comprise an implant or scaffold 510 supported on the engagement section 502. Further, the assembly can comprise a first elongate member 520 and a second elongate member 522 configured to engage with the scaffold 510. As shown, a distal portion 530 of the elongate member 520 can engage a proximal portion 540 of scaffold 510 and a distal portion 532 of the elongate member 522 can engage with a distal portion 542 of the scaffold 510.

Accordingly, in embodiments that comprise two elongate members, the elongate members can be actuated independently of each other in order to control the release of the respective proximal or distal sections 310, 312 of the scaffold 302 or implant 300.

Referring again to FIG. 6A, the catheter 210 can be configured to comprise at least one aperture. For example, the catheter 210 illustrated in FIG. 6A comprises a proximal aperture 600 and a distal aperture 602. The proximal and distal aperture 600, 602 are configured to extend through the wall 402 of the catheter 210. Further, the apertures 600, 602 are configured as slots or notches that extend transversely relative to a longitudinal axis of the catheter lumen 400. The apertures 600, 602 can extend radially at least partially into the lumen 400, and as illustrated, can extend about halfway across a diameter of the lumen 400. In some embodiments, the aperture 600, 602 can extend radially through from about ¼ to about ¾ of the diameter of the lumen 400, through from about ⅓ to about ⅔ of the diameter of the lumen 400, or in some embodiments, through about ½ of the diameter of the lumen 400.

For example, as illustrated in FIG. 6B, some embodiments can be configured such that at least one of the proximal or distal sections 310, 312 of the scaffold 302 extends within the respective proximal or distal aperture 600, 602 of the catheter 210.

Further, FIG. 6B also illustrates the scaffold 302 of the implant 300 in a mounted, collapsed, or wound position. In the mounted, collapsed, or wound position, the scaffold 302 can be wound around the catheter distal portion with about 10 to about 25 winds, from about 15 to about 20 winds, or in some embodiments about 16 or about 19 winds. Thus, before the scaffold 302 or stent 300 is released, the scaffold 302 is helically wound tightly around the catheter 210. The winding of the scaffold 302 about the catheter distal portion can put the scaffold 302 into a stressed state. As discussed further below, the scaffold 302 will tend to rebound or expand from the stressed, mounted, collapsed, or wound position.

Additionally, some embodiments can be configured such that an elongate member extends through the catheter lumen and between at least one of the proximal or distal sections of the scaffold and the wall of the catheter. For example, the elongate member can be disposed radially between the proximal or distal section of the scaffold and the wall of the catheter.

For example, FIG. 6C illustrates the configuration of the catheter 302 and the aperture 600 in relation to the elongate member 420 and the proximal section 310 of the scaffold 302. As shown, the proximal section 310 can sit within the aperture 600 and provide enough clearance between the proximal section 310 and wall 402 or the inner surface of the wall 402 such that the elongate member 420 can be positioned intermediate the wall 402 and the proximal section 310. As also shown, the proximal section 310 can extend across the entire diameter of the lumen 400 and a transverse direction. However, the proximal and/or distal sections 310, 312 can also be configured to extend across the lumen 400 less than a diameter of the lumen 400 (whether in the transverse direction or in a radial direction).

Accordingly, the elongate member 420 can secure the proximal section 310 within the aperture 600 to prevent movement of the proximal section in an axial direction 646 (shown in FIG. 6A) and/or a radial direction 648 (shown in FIG. 6C). In some embodiments, the scaffold 302 can be a resilient or self expanding scaffold, such that the proximal section 310 will tend to expand or move out of the aperture 600 without the presence of the elongate member 420. Thus, when the elongate member 420 is in place between the proximal section 310 and the wall 402 of the catheter 210, the proximal section 310 can be retained or engaged within the aperture 600.

The engagement illustrated in FIG. 6C between the proximal section 310, the elongate member 420, and the aperture 600 can also be present at the distal end of the scaffold 302, although it will not be discussed further herein. However, as noted, some embodiments can be implemented in which a single end of the scaffold is retained within an aperture or otherwise engaged by the elongate member.

Additionally, FIGS. 6A and 6C illustrate that the reduced cross-sectional segments 320, 322 can be positioned within the respective apertures 600, 602. For example, the reduced cross-sectional segments 320, 322 and the respective apertures 600, 602 can each have substantially equal lengths, measured in the direction transverse to an axis of the lumen 400. Thus, a given reduced cross-sectional segment can be seated or received into a respective aperture and achieve a fit with the aperture such that the respective proximal or distal section of the scaffold is generally restrained against movement or rotation in a direction 650 transverse to an axis of the lumen 400.

For example in some embodiments, the proximal and/or distal sections 310, 312 can comprise planar portions, as illustrated in discussed above with respect to FIG. 5. Additionally, as also shown in FIG. 5 the proximal and/or distal sections 310 can comprise an end or tab 640, 642 extending therefrom. The tabs 640, 642 can be formed at the distal ends of the proximal and distal sections 310, 312. The tabs 640, 642 can also be larger than the section of the proximal or distal section 310, 312 extending through the aperture 600, 602 (which can be the reduced cross-sectional segments 320, 322, in some embodiments).

For example, the tabs 640, 642 can be a portion of the proximal and distal sections 310, 312 that remains or exists in the presence of the reduced cross-sectional segments 320, 322. The tabs 640, 642 can protrude and create an interference against the outer surface of the catheter 210 in order to block or inhibit motion of the respective proximal or distal section 310, 312. For example, the tabs 640, 642 can be configured to extend out of the apertures 600, 602 and to abut an outer surface of the catheter 210, thereby generally restricting movement or rotation of the respective proximal or distal section of the scaffold in a direction 650 transverse to an axis of the lumen 400.

Accordingly, some embodiments can be configured such that the proximal and/or distal sections 310, 312 can be constrained against movement in an axial direction 646, a radial direction 648, and a transverse direction 650. Thus, when the implant 300 or scaffold 302 is coiled about the engagement section 216 of the catheter 210, the proximal and distal sections 310, 312 of the scaffold 302 can be secured in various directions to be engaged during delivery of the implant 300 to the treatment site. When the implant 300 reaches the treatment site, the implant 300 can then be expanded.

Figure 6D:
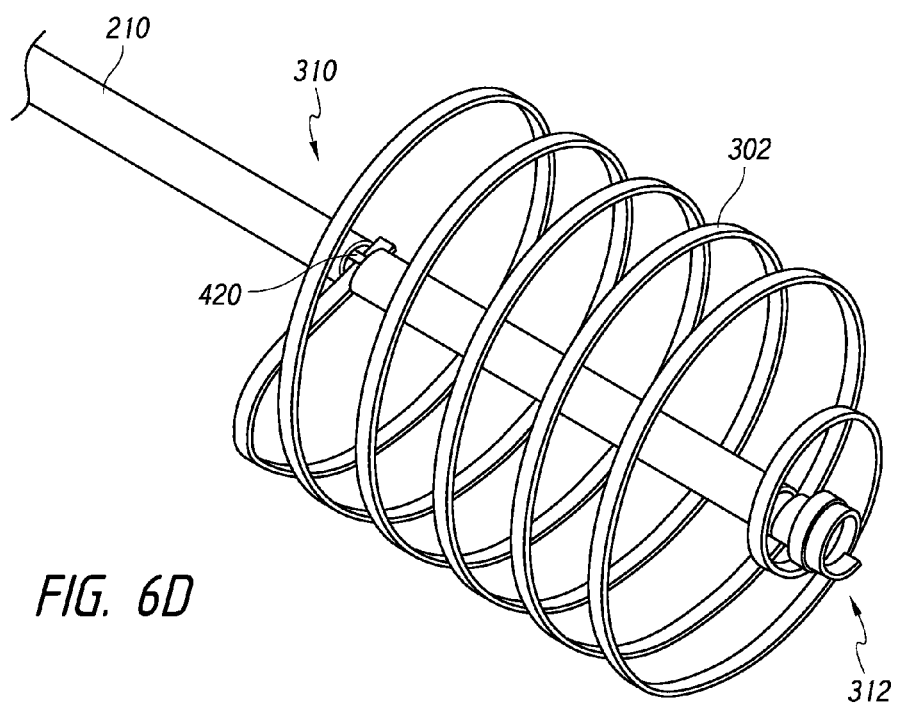

An initial phase of the implant expansion is illustrated in FIG. 6D. As shown, the proximal portion 310 of the scaffold 302 is engaged or retained by an elongate member 420. However, the scaffold 302 has expanded from a mounted or collapsed state (shown in FIG. 6B) to an expanded state (shown in FIG. 6D) because the distal section 312 of the scaffold 302 has been released from engagement with the catheter 210. When released, the stress in the wound scaffold 302 can be released as the implant distal section 312 unwinds (perhaps along with a portion of the scaffold 302 intermediate the proximal and distal sections 310, 312). For example, the distal and proximal sections 310, 312 can rotate or unwind relative to each other, allowing the diameter of the implant 300 to expand while it unwinds or rotates. The scaffold 302 can have fewer winds in the expanded position when the scaffold 302 has achieved a target diameter (likely configured to be slightly larger than the interior dimensions of the target vessel to allow the implant 300 to be urged into contact with the vessel wall). For example, in the expanded, unwound position, the scaffold 302 can have from about 4 to about 10 winds, from about 5 to about 8 winds, and in some embodiment about 6 or about 7 winds.

Thereafter, in order to fully release the scaffold 302, the engagement member 420 can be moved (either proximally or distally, depending on the configuration of the engagement member 420) in order to disengage from the proximal section 310 of the scaffold 302.

Figure 7A:
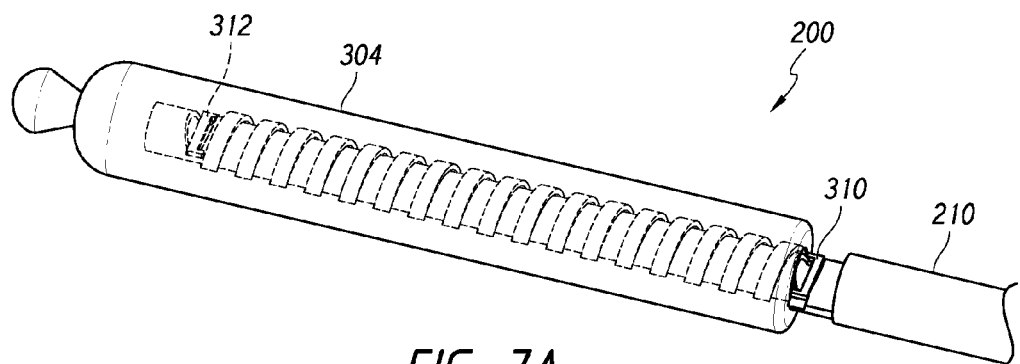
FIG. 7A-7B illustrate perspective views of an implant in a mounted or collapsed position on a catheter, according to some embodiments.
Figure 7B:
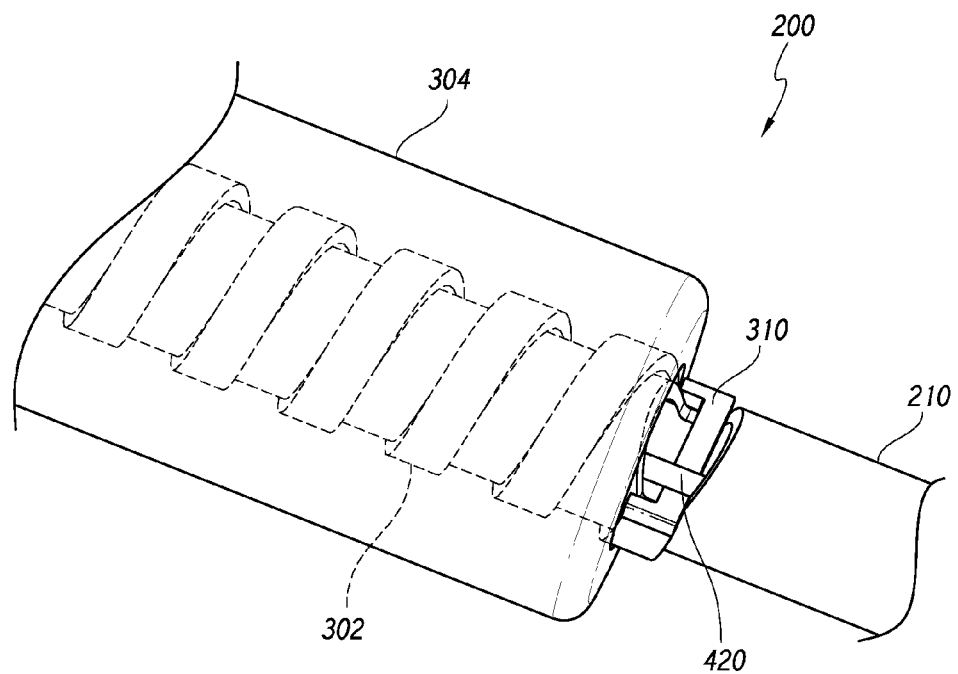
Figure 9A:
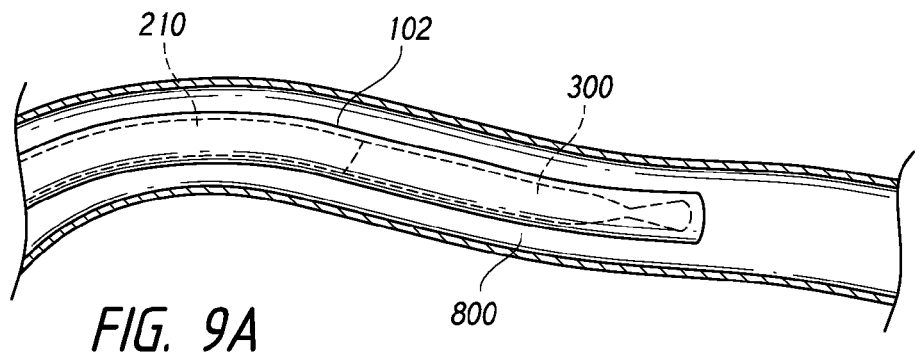
FIG. 9A-9D are sequential views of the expansion process of an implant, according to some embodiments.
Figure 9B:
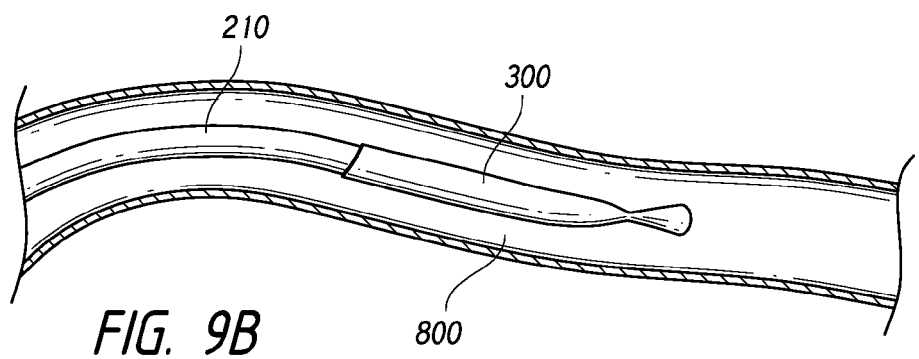
Figure 9C:
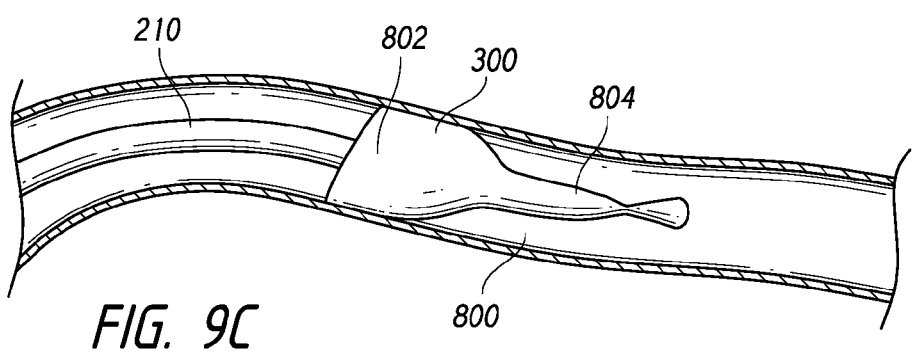
Figure 9D:
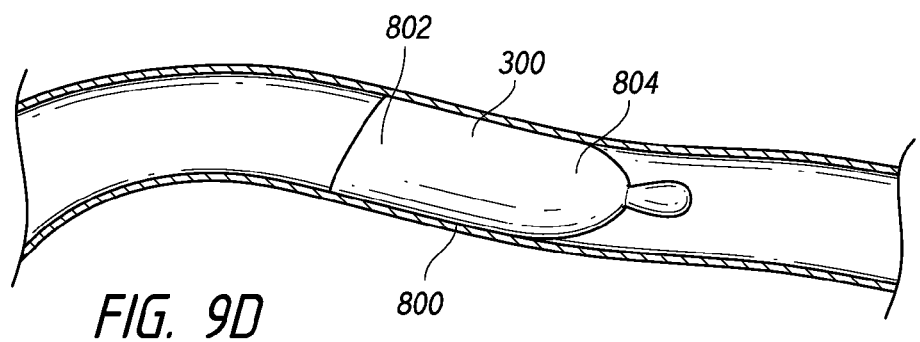

FIGS. 7A-7B illustrate perspective views of the implant carrier assembly 200, similar to the illustrations of FIGS. 6A-6B, but further including the implant membrane 304. As illustrated, the implant membrane can be positioned over the scaffold 302 and delivered in a mounted or collapsed state. The elongate member 420 can be engaged with the proximal section 310 of the scaffold 302. Further, as noted above, the elongate member 420 or a different elongate member can be engaged with the distal section 312 of the scaffold 302.

Referring now to FIG. 8, the implant carrier assembly 200 can also comprise the handle assembly 250. The handle assembly 250 can be used to deploy the proximal and distal sections 310, 312 of the implant 300. In some embodiments, the assembly 250 can include a deployment handle or body 700 with a side port 702 to accommodate syringe attachment to flush the catheter 210 of air and to pre-expand the membrane 304 before deploying the implant 300.

The handle assembly 250 can also comprise at least one slider member configured to actuate an elongate member of the assembly 200. In the embodiment illustrated in FIG. 10, the handle assembly 250 can also be configured to comprise more than one slider member. As illustrated, the handle assembly 250 comprises first and second slider members 710, 712. The first and second slider members 710, 712 can be coupled to respective elongate members, such as elongate members 522, 520 of the embodiment illustrated in FIG. 6B.

Additionally, in accordance with some embodiments, the handle assembly 250 can also comprise one or more retention clips 720, 722. The retention clips 720, 722 can be configured to prevent movement of the slider members 710, 712 relative to the handle 700, thereby restricting movement of the elongate members 520, 522 and premature deployment of the implant. When the retention clips 720, 722 are removed, which may be done separately or together, the slider members 710, 712 can be used to release the proximal and distal ends of the implant. For example, the proximal slider member 710 can be configured to release the proximal end of the implant. Further, the distal slider member 712 can be configured to release the distal end of the implant.

Implant deployment can be performed as a two stage process, which is illustrated in FIGS. 9A-9D. The guide catheter 102 and implant can first be moved to a target location 800 (shown FIG. 9A). The guide catheter 102 can then be removed (shown in FIG. 9B). After the proximal-most retention clip is removed from the handle assembly, the proximal slider member of the handle assembly can be pulled proximally to release a proximal end 802 of the implant 300 (shown in FIG. 9C). When the proximal implant end 802 is released, the physician can check the implant position and observe as the inner space of the implant 300 fills with blood. Some slight movement of the implant 300 may be helpful to achieve precise placement. The second retention clip of the handle assembly can then be removed and the distal slider member of the handle assembly can be pulled proximally to release a distal end 804 of the implant (shown in FIG. 9D), thus releasing the entire implant 300.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the inventions have been described, these have been presented by way of example only, and are not intended to limit the scope of the inventions. Indeed, the novel methods and systems described herein may be embodied in a variety of other forms without departing from the spirit thereof. The accompanying claims and their equivalents are intended to cover such forms or modifications as would fall within the scope and spirit of the inventions.

What is claimed is:

1. An occlusion device delivery system, comprising:
a catheter having a central axis and a lumen extending along the central axis between distal and proximal sections, the distal section having proximal and distal apertures extending through a wall of the catheter;
a helical implant carried on the catheter and comprising proximal and distal segments configured to extend within the respective proximal and distal apertures, the proximal segment having a first end whereat the implant changes in curvature and a second end whereat the implant terminates, the distal segment having a first end whereat the implant changes in curvature and a second end whereat the implant terminates;
an elongate member extending through the lumen, wherein when engaged with the proximal segment, the elongate member extends across the proximal aperture between the catheter wall and the proximal segment to radially restrain the proximal segment within the proximal aperture while the proximal segment second end is positioned outside of the proximal aperture, and wherein when engaged with the distal segment, the elongate member extends across the distal aperture between the catheter wall and the distal segment to radially restrain the distal segment within the distal aperture while the distal segment second end is positioned outside of the distal aperture;
a handle coupled to the proximal section; and
a slider member coupled to the handle and to the elongate member, the slider member being movable to cause disengagement of the elongate member from the proximal and distal segments to permit expansion of the implant from an engaged configuration.

2. The system of claim 1, wherein the proximal segment second end has a larger cross-sectional profile than a portion of the proximal segment extending through the proximal aperture, and the distal segment second end has a larger cross-sectional profile than a portion of the distal segment extending through the proximal aperture.

3. The system of claim 1, wherein the proximal segment comprises a reduced cross-sectional segment that is configured to extend within the proximal aperture when engaged with the elongate member.

4. The system of claim 1, wherein the distal segment comprises a reduced cross-sectional segment that is configured to extend within the distal aperture when engaged with the elongate member.

5. The system of claim 4, wherein the reduced cross-sectional segment comprises a distal notch having a first longitudinal length, the distal aperture having a distal aperture length extending transverse to the catheter central axis, the first longitudinal length being substantially equal to the distal aperture length.

6. The system of claim 1, wherein the proximal and distal segments extend across the lumen less than a diameter of the lumen.

7. The system of claim 1, wherein, upon proximal withdrawal of the elongate member through the catheter lumen, the elongate member is configured to disengage and radially release the distal segment from the distal aperture.

8. The system of claim 7, wherein, upon continued proximal withdrawal of the elongate member, the elongate member is configured to disengage and radially release the proximal segment from the proximal aperture.

9. The system of claim 1, wherein the elongate member comprises a wire.

10. The system of claim 1, wherein the apertures comprise slots that are transverse to an axis of the lumen.

11. The system of claim 1, wherein the proximal segment first end comprises a proximal elbow at which the implant diverges from a helical path.

12. The system of claim 11, wherein the proximal elbow defines a substantially right angle orientation.

13. The system of claim 1, wherein the distal segment first end comprises a distal elbow at which the implant diverges from a helical path.

14. The system of claim 13, wherein the distal elbow defines a substantially right angle orientation.

15. The system of claim 1, wherein the implant changes to a smaller radius of curvature at the proximal segment first end and the distal segment first end from an intermediate portion of the implant extending between the proximal and distal segments.

16. An occlusion device delivery system, comprising:
a catheter configured to carry an implant, the catheter having distal and proximal sections, a central axis, and a lumen extending therethrough, the distal section having proximal and distal sidewall apertures extending into the lumen; and
an engagement mechanism extending within the lumen; and
a helical implant comprising proximal and distal segments each having first and second ends, the implant terminating at the second ends of the proximal and distal segments;
wherein in an engaged configuration, the proximal and distal segments extend within the proximal and distal sidewall apertures and the implant bends inwardly from a helical path toward the central axis at the first ends of the proximal and distal segments, the engagement mechanism extending between a sidewall of the catheter and the proximal and distal segments to radially restrain the proximal segment within the proximal aperture and the distal segment within the distal aperture while the second ends of the proximal and distal segments are positioned outside of the proximal and distal apertures, and wherein the engagement mechanism is movable to disengage from the proximal and distal segments and permit expansion of the implant from the engaged configuration.

17. The system of claim 16, wherein the engagement mechanism comprises a wire, and upon proximal withdrawal of the engagement mechanism through the catheter lumen, the engagement mechanism is configured to disengage and radially release the distal segment from the distal aperture.

18. The system of claim 17, wherein, upon continued proximal withdrawal of the engagement mechanism, the engagement mechanism is configured to disengage and radially release the proximal segment from the proximal aperture.

19. The system of claim 16, wherein the engagement mechanism comprises first and second wires, the first wire being coupled to a first handle and the second wire being coupled to a second handle, the first and second handles being movable to cause disengagement of the proximal and distal segments of the implant.

20. The system of claim 16, wherein the proximal segment first end comprises a proximal elbow at which the implant diverges from a helical path.

21. The system of claim 20, wherein the proximal elbow defines a substantially right angle orientation.

22. The system of claim 16, wherein the distal segment first end comprises a distal elbow at which the implant diverges from a helical path.

23. The system of claim 22, wherein the distal elbow defines a substantially right angle orientation.

* * * * *